United States Patent
Okazaki et al.

(10) Patent No.: US 6,939,887 B2
(45) Date of Patent: Sep. 6, 2005

(54) BENZIMIDAZOLIDINONE DERIVATIVES

(75) Inventors: Kazuhiko Okazaki, Nishinomiya (JP); Yasuyuki Ueki, Sanda (JP)

(73) Assignee: Sumitomo Pharmaceuticals Co., Ltd., Osaka (JP)

( * ) Notice: Subject to any disclaimer, the term of this patent is extended or adjusted under 35 U.S.C. 154(b) by 0 days.

(21) Appl. No.: 10/470,813

(22) PCT Filed: Jan. 30, 2002

(86) PCT No.: PCT/JP02/00692
§ 371 (c)(1), (2), (4) Date: Jul. 30, 2003

(87) PCT Pub. No.: WO02/060878
PCT Pub. Date: Aug. 8, 2002

(65) Prior Publication Data
US 2004/0142850 A1 Jul. 22, 2004

(30) Foreign Application Priority Data
Jan. 30, 2001 (JP) .................................. 2001-022352

(51) Int. Cl.⁷ .................. A61K 31/4184; C07D 235/26
(52) U.S. Cl. .................................. 514/387; 548/306.4
(58) Field of Search ........................ 548/306.4; 514/387

(56) References Cited

U.S. PATENT DOCUMENTS

| | | | |
|---|---|---|---|
| 4,200,641 A | 4/1980 | Vandenberk et al. | |
| 6,075,039 A | 6/2000 | Gallagher et al. | |
| 6,576,656 B1 | 6/2003 | Tokunaga et al. | |
| 6,582,351 B1 * | 6/2003 | Sawada et al. | 546/118 |

FOREIGN PATENT DOCUMENTS

| | | |
|---|---|---|
| DE | 27 14 437 A1 | 10/1977 |
| WO | WO 00/10975 A1 | 3/2000 |

OTHER PUBLICATIONS

"Reach–through Claims", Baker Botts LLP/News & Events/In Print, Apr. 12, 2002, http://www.bakerbotts.com/news.*

* cited by examiner

*Primary Examiner*—Joseph K. McKane
*Assistant Examiner*—Janet L Coppins
(74) *Attorney, Agent, or Firm*—Leydig, Voit & Mayer, Ltd.

(57) ABSTRACT

The present invention can provide novel compounds useful as orally administrable growth hormone releaser, more specifically a benzimidazolidinone derivative of formula (1) or a pharmaceutically acceptable salt thereof:

(1) wherein $R^1$ is optionally substituted alkyl or the like; $R^2$, $R^3$ and $R^4$ are each hydrogen, optionally substituted alkyl, or the like;

$R^5$ is optionally substituted aryl; q is 0 or 1; and $W^1$ is a group represented by formula (2): (2) n is 1, 2 or 3; m is 0, 1, 2 or 3;

$R^6$ and $R^7$ are each hydrogen, optionally substituted alkyl, or the like; and $R^8$ and $R^9$ are each hydrogen, optionally substituted alkyl, or the like.

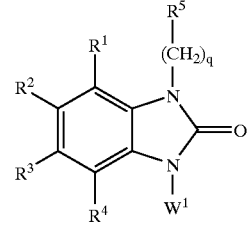

(1)

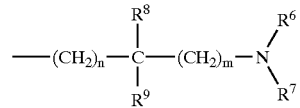

(2)

12 Claims, No Drawings

BENZIMIDAZOLIDINONE DERIVATIVES

TECHNICAL FIELD TO WHICH THE INVENTION BELONGS

The present invention relates to novel benzimidazolidinone derivatives useful as a growth hormone releaser and the like.

BACKGROUND ART

Various factors are involved in the growth of individuals. Particularly, growth hormone plays the most important role in the growth. Growth hormone deficiency, wherein secretion of growth hormone is insufficient, develops symptoms of dwarfism. Furthermore, growth hormone is known to have effects on the metabolic processes of the body: increased rate of protein synthesis, decreased rate of carbohydrate utilization, increased mobilization of free fatty acids and use of fatty acids and the like.

Various substances such as arginine, L-3,4-dihydroxyphenylalanine (L-DOPA), glucagon, vasopressin, insulin and the like are known to cause release of growth hormone. Activities such as sleep and exercise are also known to cause release of growth hormone. It is also known that these substances and activities cause release of growth hormone from the pituitary by acting on the hypothalamus by way of decreasing somatostatin secretion, increasing secretion of known growth hormone releasing factors (GRF) or an unknown endogenous growth hormone releasing factors and the like.

As a way to increase the level of growth hormone in the body, administration of growth hormone itself for supplementation is known. As the growth hormone, recombinant products are currently used in general. Growth hormone cannot be given orally because it is a protein.

A second way to increase the level of growth hormone in the body is to endogenously increase the level of growth hormone. That is, GRF, its derivatives (Schoen W. R. et. al., "Growth hormone secretagogues" in Annual Reports in Medicinal Chemistry:Academic Press, Vol.28, Chapter 19, 1993) or peptides that stimulate production and release of growth hormone (U.S. Pat. No. 4,411,890) is administered to cause endogenous secretion of growth hormone, thereby to increase the level of the growth hormone. While these peptides have smaller molecular weight as compared to growth hormone, they are still problematic in that they are not suitable for oral administration.

GB 2,297,972 and WO 00/10975 disclose non-peptide compounds useful as growth hormone releasers.

DISCLOSURE OF THE INVENTION

The problem to be solved by the invention is provision of an orally administrable growth hormone releaser.

The inventors of the present invention have intensively carried out research in order to solve the above problem, and found that benzimidazolidinone derivatives and pharmaceutically acceptable salts thereof promote secretion of growth hormone, which resulted in the completion of the present invention. The benzimidazolidinone derivatives of the present invention are non-peptidic compounds with low molecular weight and become orally administrable growth hormone releasers.

That is, the present invention is as follows.
[1] A benzimidazolidinone derivative of formula (1) or a pharmaceutically acceptable salt thereof:

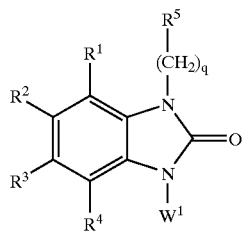

(1)

wherein
$R^1$ is optionally substituted $C_1$–$C_3$ alkyl, optionally substituted $C_1$–$C_3$ alkoxy, $C_1$–$C_3$ alkylthio, hydroxy, cyano, halogen or nitro;
$R^2$ is hydrogen, optionally substituted $C_1$–$C_3$ alkyl, optionally substituted $C_1$–$C_3$ alkoxy, hydroxy, cyano or halogen;
$R^3$ is hydrogen, optionally substituted $C_1$–$C_6$ alkyl, optionally substituted $C_3$–$C_7$ alkynyl, optionally substituted $C_1$–$C_6$ alkoxy, carbamoyl, amino, hydroxy, cyano, nitro or halogen;
$R^4$ is hydrogen, hydroxy, cyano, fluorine or chlorine;
q is 0 or 1;
$R^5$ is optionally substituted aryl;
$W^1$ is a group represented by formula (2):

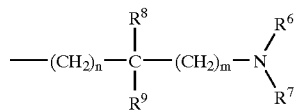

(2)

wherein
n is 1, 2 or 3; m is 0, 1, 2, or 3;
$R^6$ and $R^7$ are each independently hydrogen, optionally substituted alkyl or optionally substituted cycloalkyl; or
$R^6$ and $R^7$ are taken together to form optionally substituted saturated heterocyclic ring containing nitrogen(s);
$R^8$ and $R^9$ are each independently hydrogen, optionally substituted alkyl or optionally substituted cycloalkyl; or
$R^8$ and $R^9$ are taken together to form optionally substituted cycloalkane or optionally substituted saturated heterocyclic ring;
or $R^6$ and $R^8$ are taken together to form optionally substituted saturated heterocyclic ring containing nitrogen(s); or $R^7$ and $R^9$ are taken together to form optionally substituted saturated heterocyclic ring containing nitrogen(s).
[2] The benzimidazolidinone derivative or a pharmaceutically acceptable salt thereof according to [1] above, wherein $R^1$ is optionally substituted $C_1$–$C_3$ alkyl.
[3] The benzimidazolidinone derivative or a pharmaceutically acceptable salt thereof according to [1] above, wherein $R^1$ is $C_1$–$C_3$ alkyl substituted by halogen(s).
[4] The benzimidazolidinone derivative or a pharmaceutically acceptable salt thereof according to any of [1] to [3] above, wherein both of $R^2$ and $R^4$ are hydrogen.
[5] The benzimidazolidinone derivative or a pharmaceutically acceptable salt thereof according to any of [1] to [4] above, wherein $R^3$ is optionally substituted $C_3$–$C_7$ alkynyl or carbamoyl.

[6] The benzimidazolidinone derivative or a pharmaceutically acceptable salt thereof according to any of [1] to [5] above, wherein $R^5$ is optionally substituted phenyl, optionally substituted 1-naphthyl or optionally substituted 2-naphthyl.

[7] The benzimidazolidinone derivative or a pharmaceutically acceptable salt thereof according to [6] above, wherein $R^5$ is phenyl substituted by alkyl(s), halogen(s), trifluoromethyl(s) or alkoxy(s).

[8] The benzimidazolidinone derivative or a pharmaceutically acceptable salt thereof according to any of [1] to [6] above, wherein $R^6$ and $R^7$ are each independently optionally substituted alkyl or optionally substituted cycloalkyl; or $R^6$ and $R^7$ are taken together to form optionally substituted saturated heterocyclic ring containing nitrogen(s).

[9] The benzimidazolidinone derivative or a pharmaceutically acceptable salt thereof according to any of [1] to [7] above, wherein $W^1$ is a group represented by formula (3):

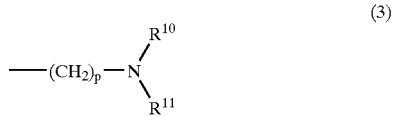

wherein p is 2, 3 or 4; $R^{10}$ and $R^{11}$ are each independently optionally substituted alkyl.

[10] The benzimidazolidinone derivative or a pharmaceutically acceptable salt thereof according to [9] above, wherein $R^{10}$ and $R^{11}$ are each independently methyl or ethyl.

[11] The benzimidazolidinone derivative or a pharmaceutically acceptable salt thereof according to [1] above, wherein $R^1$ is trifluoromethyl.

[12] The benzimidazolidinone derivative or a pharmaceutically acceptable salt thereof according to [1] or [11] above, wherein $R^3$ is carbamoyl.

[13] The benzimidazolidinone derivative or a pharmaceutically acceptable salt thereof according to [1] above, wherein $R^1$ is trifluoromethyl, $R^2$ is hydrogen, $R^3$ is carbamoyl, and $R^4$ is hydrogen.

[14] The benzimidazolidinone derivative or a pharmaceutically acceptable salt thereof according to [1] above, wherein $R^1$ is trifluoromethyl, $R^2$ is hydrogen, $R^3$ is carbamoyl, $R^4$ is hydrogen and $W^1$ is 2-(diethylamino)ethyl.

[15] A medicament comprising a benzimidazolidinone derivative or a pharmaceutically acceptable salt thereof according to any one of [1] to [14] above.

[16] The medicament according to [15] above, wherein the medicament is a growth hormone releaser.

DETAILED DESCRIPTION OF THE INVENTION

The meanings or definitions of the terms used in the present specification are as follows.

The alkyl moiety of the "optionally substituted $C_1$–$C_3$ alkyl" in $R^1$ and $R^2$ includes, for example, a straight chain or branched chain $C_1$–$C_3$ alkyl, such as methyl, ethyl, propyl, 2-propyl, etc.

The substituent of the "optionally substituted $C_1$–$C_3$ alkyl" in $R^1$ and $R^2$ includes halogen atom (for example, fluorine, chlorine, bromine, iodine), hydroxy, amino, alkylamino (for example, $C_1$–$C_3$ alkylamino such as methylamino, ethylamino, propylamino, etc.), dialkylamino (for example, $C_2$–$C_6$ dialkylamino such as dimethylamino, diethylamino, ethylmethylamino, dipropylamino, etc.), cyano, carbamoyl, etc. The number of the substituents is one or more. Typical examples of substituted alkyl in $R^1$ and $R^2$ are trifluoromethyl, fluoromethyl, difluoromethyl, hydroxymethyl, aminomethyl, carbamoylmethyl and the like.

The alkoxy moiety of the "optionally substituted $C_1$–$C_3$ alkoxy" in $R^1$ and $R^2$ includes, for example, a straight chain or branched chain $C_1$–$C_3$ alkoxy, such as methoxy, ethoxy, propoxy, 2-propoxy, etc.

The substituent of the "optionally substituted $C_1$–$C_3$ alkoxy" in $R^1$ and $R^2$ includes halogen atom (for example, fluorine, chlorine, bromine, iodine), hydroxy, amino, alkylamino (for example, $C_1$–$C_3$ alkylamino such as methylamino, ethylamino, propylamino, etc.), dialkylamino (for example, $C_2$–$C_6$ dialkylamino such as dimethylamino, diethylamino, ethylmethylamino, dipropylamino, etc.), carbamoyl, etc. The number of the substituents is one or more.

The "$C_1$–$C_3$ alkylthio" in $R^1$ includes, for example, a straight chain $C_1$–$C_3$ alkylthio, such as methylthio, ethylthio, propylthio, etc.

The "halogen" in $R^1$, $R^2$ and $R^3$ includes, for example, fluorine, chlorine, bromine and iodine.

The alkyl moiety of the "optionally substituted $C_1$–$C_6$ alkyl" in $R^3$ includes, for example, a straight chain or branched chain $C_1$–$C_6$ alkyl, such as methyl, ethyl, propyl, 1-methylethyl, butyl, 2-methylpropyl, pentyl, 3-methylbutyl, hexyl, etc.

The substituent of the "optionally substituted $C_1$–$C_6$ alkyl" in $R^3$ includes halogen atom (for example, fluorine, chlorine, bromine, iodine), hydroxy, amino, alkylamino (for example, $C_1$–$C_3$ alkylamino such as methylamino, ethylamino, propylamino, etc.), dialkylamino (for example, $C_2$–$C_6$ dialkylamino such as dimethylamino, diethylamino, ethylmethylamino, dipropylamino, etc.), cyano, carbamoyl, etc. The number of the substituents is one or more.

The alkynyl moiety of the "optionally substituted $C_3$–$C_7$ alkynyl" in $R^3$ includes, for example, a $C_3$–$C_7$ alkynyl with one triple bond, such as 1-propynyl, 2-propynyl, 1-butynyl, 1-pentynyl, etc.

The substituent of the "optionally substituted $C_3$–$C_7$ alkynyl" in $R^3$ includes hydroxy, amino, alkylamino (for example, $C_1$–$C_3$ alkylamino such as methylamino, ethylamino, propylamino, etc.), dialkylamino (for example, $C_2$–$C_6$ dialkylamino such as dimethylamino, diethylamino, ethylmethylamino, dipropylamino, etc.), cyano, carbamoyl, $C_2$–$C_4$ alkylcarbamoyl (methylcarbamoyl, ethylcarbamoyl, propylcarbamoyl, etc.), $C_3$–$C_7$ dialkylcarbamoyl (dimethylcarbamoyl, diethylcarbamoyl, ethylmethylcarbamoyl, dipropylcarbamoyl, etc.), N-(heterocyclic ring containing nitrogen(s)) carbonyl group (the heterocyclic ring containing nitrogen(s) includes, for example, 5-, 6- or 7-membered ring containing 1 or 2 nitrogen atoms and 0 or 1 oxygen atom such as pyrrolidine, piperazine, morpholine, etc. Typical examples of N-(heterocyclic ring containing nitrogen(s)) carbonyl group are N-pyrrolidinylcarbonyl, N-piperazinylcarbonyl, 4-morpholinylcarbonyl and the like), $C_3$–$C_5$ alkylcarbamoyl substituted by hydroxy (for example, 2-hydroxyethylcarbamoyl, 3-hydroxypropylcarbamoyl, etc.), $C_4$–$C_8$ dialkylcarbamoyl substituted by hydroxy (for example, 2-hydroxyethylmethylcarbamoyl, 2-hydroxyethylethylcarbamoyl, 3-hydroxypropylmethylcarbamoyl, 3-hydroxypropylethylcarbamoyl, 3-hydroxypropylpropylcarbamoyl, etc.), sulfamoyl, $C_1$–$C_3$ alkylsulfamoyl (for example, methylsulfamoyl, ethylsulfamoyl, propylsulfamoyl, etc.), $C_2$–$C_4$ alkylureido (for example, methylureido, ethylureido, propylureido, etc.), $C_3$–$C_7$ dialkylureido (for example, dimethylureido, diethylureido, ethylmethylureido, dipropylureido, etc.), etc. The number of the substituents is one or more.

The alkoxy moiety of the "optionally substituted $C_1$–$C_6$ alkoxy" in $R^3$ includes, for example, a straight chain or branched chain $C_1$–$C_6$ alkoxy, such as methoxy, ethoxy, propoxy, 2-propoxy, butoxy, 2-butoxy, pentoxy, 2-pentoxy, hexoxy, 2-hexoxy, etc.

The substituent of the "optionally substituted $C_1$–$C_6$ alkoxy" in $R^3$ includes halogen atom (for example, fluorine, chlorine, bromine, iodine), hydroxy, amino, alkylamino (for example, $C_1$–$C_3$ alkylamino such as methylamino, ethylamino, propylamino, etc.), dialkylamino (for example, $C_2$–$C_6$ dialkylamino such as dimethylamino, diethylamino, ethylmethylamino, dipropylamino, etc.), carbamoyl, etc. The number of the substituents is one or more.

The aryl moiety of the "optionally substituted aryl" in $R^5$ includes, for example, $C_6$–$C_{10}$ aryl such as phenyl, naphthyl (for example, 1-naphthyl, 2-naphthyl, etc.), etc.

The substituent of the "optionally substituted aryl" in $R^5$ includes, for example, halogen atom (for example, fluorine, chlorine, bromine, etc.), alkyl (for example, $C_1$–$C_3$ alkyl such as methyl, ethyl, propyl, etc.), substituted $C_1$–$C_3$ alkyl (the substituent includes halogen atom (for example, fluorine, chlorine, bromine, etc.), amino, hydroxy, etc. Typical examples are trifluoromethyl and the like.), alkoxy (for example, $C_1$–$C_3$ alkoxy such as methoxy, ethoxy, propoxy, etc. The neighboring alkoxys may be taken together to form methylenedioxy or ethylenedioxy.), substituted $C_1$–$C_3$ alkoxy (the substituent includes halogen atom (for example, fluorine, chlorine, bromine, etc.), amino, hydroxy, etc.), substituted phenyl (the substituent includes, for example, halogen atom (for example, fluorine, chlorine, bromine, etc.), $C_1$–$C_3$ alkyl (for example, methyl, ethyl, propyl, etc.), substituted $C_1$–$C_3$ alkyl (the substituent includes halogen atom (for example, fluorine, chlorine, bromine, etc.), amino, etc.), $C_1$–$C_3$ alkoxy (for example, methoxy, ethoxy, propoxy, etc.), substituted $C_1$–$C_3$ alkoxy (the substituent includes halogen atom (for example, fluorine, chlorine, bromine, etc.), etc.)), etc. The substituted aryl may have one or more substituents. The substituted alkyl, the substituted alkoxy and the substituted phenyl, which are the substituents of aryl, may have one or more substituents. The substituted alkyl and the substituted alkoxy, which are the substituents of phenyl that substitutes aryl, may have one or more substituents.

The alkyl moiety of the "optionally substituted alkyl" in $R^6$ and $R^7$ includes, for example, a straight chain or branched chain $C_1$–$C_6$ alkyl, such as methyl, ethyl, propyl, 2-propyl, butyl, 2-methylpropyl, 1-methylpropyl, pentyl, 3-methylbutyl, hexyl, etc.

The substituent of the "optionally substituted $C_1$–$C_6$ alkyl" in $R^6$ and $R^7$ includes halogen atom (for example, fluorine, chlorine, bromine, iodine), hydroxy, amino, alkylamino (for example, $C_1$–$C_3$ alkylamino such as methylamino, ethylamino, propylamino, etc.), dialkylamino (for example, $C_2$–$C_6$ dialkylamino such as dimethylamino, diethylamino, ethylmethylamino, dipropylamino, etc.), cyano, carbamoyl, etc. The number of the substituents is one or more.

The cycloalkyl moiety of the "optionally substituted cycloalkyl" in $R^6$ and $R^7$ includes, for example, $C_3$–$C_7$ cycloalkyl, such as cyclopropyl, cyclobutyl, cyclopentyl, cyclohexyl, cycloheptyl, etc.

The substituent of the "optionally substituted $C_3$–$C_7$ cycloalkyl" in $R^6$ and $R^7$ includes halogen atom (for example, fluorine, chlorine, bromine, iodine), hydroxy, amino, alkylamino (for example, $C_1$–$C_3$ alkylamino such as methylamino, ethylamino, propylamino, etc.), dialkylamino (for example, $C_2$–$C_6$ dialkylamino such as dimethylamino, diethylamino, ethylmethylamino, dipropylamino, etc.), cyano, carbamoyl, etc. The number of the substituents is one or more.

The saturated heterocyclic ring containing nitrogen(s) moiety of the "optionally substituted saturated heterocyclic ring containing nitrogen(s)" which $R^6$ and $R^7$ are taken together to form, includes, for example, 5-, 6- or 7-membered heterocyclic ring containing 1 or 2 nitrogen atoms and 0 or 1 oxygen atom, such as pyrrolidine, piperazine, morpholine, etc.

The substituent of the "optionally substituted saturated heterocyclic ring containing nitrogen(s)" which $R^6$ and $R^7$ are taken together to form, includes, for example, halogen atom (for example, fluorine, chlorine, bromine, iodine), hydroxy, amino, alkylamino (for example, $C_1$–$C_3$ alkylamino such as methylamino, ethylamino, propylamino, etc.), dialkylamino (for example, $C_2$–$C_6$ dialkylamino such as dimethylamino, diethylamino, ethylmethylamino, dipropylamino, etc.), cyano, carbamoyl, etc. The number of the substituents is one or more.

The alkyl moiety of the "optionally substituted alkyl" in $R^8$ and $R^9$ includes, for example, a straight chain or branched chain $C_1$–$C_6$ alkyl, such as methyl, ethyl, propyl, 1-methylethyl, butyl, 2-methylpropyl, 1-methylpropyl, pentyl, 3-methylbutyl, hexyl, etc.

The substituent of the "optionally substituted $C_1$–$C_6$ alkyl" in $R^8$ and $R^9$ includes halogen atom (for example, fluorine, chlorine, bromine, iodine), hydroxy, amino, alkylamino (for example, $C_1$–$C_3$ alkylamino such as methylamino, ethylamino, propylamino, etc.), dialkylamino (for example, $C_2$–$C_6$ dialkylamino such as dimethylamino, diethylamino, ethylmethylamino, dipropylamino, etc.), cyano, carbamoyl, etc. The number of the substituents is one or more.

The cycloalkyl moiety of the "optionally substituted cycloalkyl" in $R^8$ and $R^9$ includes, for example, $C_3$–$C_7$ cycloalkyl, such as cyclopropyl, cyclobutyl, cyclopentyl, cyclohexyl, cycloheptyl, etc.

The substituent of the "optionally substituted $C_3$–$C_7$ cycloalkyl" in $R^8$ and $R^9$ includes halogen atom (for example, fluorine, chlorine, bromine, iodine), hydroxy, amino, alkylamino (for example, $C_1$–$C_3$ alkylamino such as methylamino, ethylamino, propylamino, etc.), dialkylamino (for example, $C_2$–$C_6$ dialkylamino such as dimethylamino, diethylamino, ethylmethylamino, dipropylamino, etc.), cyano, carbamoyl, etc. The number of the substituents is one or more.

The cycloalkane moiety of the "optionally substituted cycloalkane" which $R^8$ and $R^9$ are taken together to form, includes, for example, $C_3$–$C_7$ cycloalkane such as cyclopropane, cyclobutane, cyclopentane, cyclohexane, cycloheptane, etc.

The substituent of the "optionally substituted cycloalkane" which $R^8$ and $R^9$ are taken together to form, includes, for example, halogen atom (for example, fluorine, chlorine, bromine, iodine), hydroxy, amino, alkylamino (for example, $C_1$–$C_3$ alkylamino such as methylamino, ethylamino, propylamino, etc.), dialkylamino (for example, $C_2$–$C_6$ dialkylamino such as dimethylamino, diethylamino, ethylmethylamino, dipropylamino, etc.), cyano, carbamoyl, etc. The number of the substituents is one or more.

The saturated heterocyclic ring moiety of the "optionally substituted saturated heterocyclic ring" which $R^8$ and $R^9$ are taken together to form, includes, for example, 5-, 6- or 7-membered heterocyclic ring containing 1 or 2 nitrogen atoms and 0 or 1 oxygen atom such as pyrrolidine, piperazine, morpholine, etc.

The substituent of the "optionally substituted saturated heterocyclic ring" which $R^8$ and $R^9$ are taken together to form, includes, for example, halogen atom (for example, fluorine, chlorine, bromine, iodine), hydroxy, amino, alkylamino (for example, $C_1$–$C_3$ alkylamino such as methylamino, ethylamino, propylamino, etc.), dialkylamino (for example, $C_2$–$C_6$ dialkylamino such as dimethylamino, diethylamino, ethylmethylamino, dipropylamino, etc.), cyano, carbamoyl, etc. The number of the substituents is one or more.

The saturated heterocyclic ring containing nitrogen(s) moiety of the "optionally substituted saturated heterocyclic ring containing nitrogen(s)" which $R^6$ and $R^8$ are taken together to form or the "optionally substituted saturated heterocyclic ring containing nitrogen(s)" which $R^7$ and $R^9$ are taken together to form, includes, for example, 5-, 6- or 7-membered heterocyclic ring containing 1 or 2 nitrogen atoms and 0 or 1 oxygen atom such as pyrrolidine, piperazine, morpholine, etc.

The substituent of the "optionally substituted saturated heterocyclic ring containing nitrogen(s)" which $R^6$ and $R^8$ are taken together to form and the "optionally substituted saturated heterocyclic ring containing nitrogen(s)" which $R^7$ and $R^9$ are taken together to form includes, for example, halogen atom (for example, fluorine, chlorine, bromine, iodine), hydroxy, amino, alkylamino (for example, $C_1$–$C_3$ alkylamino such as methylamino, ethylamino, propylamino, etc.), dialkylamino (for example, $C_2$–$C_6$ dialkylamino such as dimethylamino, diethylamino, ethylmethylamino, dipropylamino, etc.), cyano, carbamoyl, etc. The number of the substituents is one or more.

The alkyl moiety of the "optionally substituted alkyl" in $R^{10}$ and $R^{11}$ includes, for example, a straight chain or branched chain $C_1$–$C_6$ alkyl, such as methyl, ethyl, propyl, 2-propyl, butyl, 2-methylpropyl, 1-methylpropyl, pentyl, 3-methylbutyl, hexyl, etc.

The substituent of the "optionally substituted $C_1$–$C_6$ alkyl" in $R^{10}$ and $R^{11}$ includes halogen atom (for example, fluorine, chlorine, bromine, iodine), hydroxy, amino, alkylamino (for example, $C_1$–$C_3$ alkylamino such as methylamino, ethylamino, propylamino, etc.), dialkylamino (for example, $C_2$–$C_6$ dialkylamino such as dimethylamino, diethylamino, ethylmethylamino, dipropylamino, etc.), cyano, carbamoyl, etc. The number of the substituents is one or more.

The benzimidazolidinone derivatives of the present invention includes separated pure optical isomers, partially purified optical isomers, racemates, mixtures of diastereomers or the like.

Pharmaceutically acceptable salts of the benzimidazolidinone derivatives include, for example, salts with inorganic acids or organic acids. Examples of the inorganic acid include hydrochloric acid, hydrobromic acid, nitric acid, sulfuric acid, phosphoric acid and the like. Examples of the organic acid include formic acid, acetic acid, trifluoroacetic acid, propionic acid, lactic acid, tartaric acid, oxalic acid, fumaric acid, maleic acid, citric acid, malonic acid, methanesulfonic acid and the like. In case that the benzimidazolidinone derivatives of the present invention have acidic functional group(s) such as carboxyl group(s) and the like, salts with bases may be formed. The salts with bases include, for example, salts with basic amino acids such as arginine, lysine, and the like; alkaline metal salts such as sodium salt, potassium salt, etc.; alkaline earth metal salts such as calcium salt, magnesium salt, etc., and the like. The present invention also encompasses solvates of the benzimidazolidinone derivatives or pharmaceutically acceptable salts thereof such as a hydrate and the like.

The benzimidazolidinone derivatives of formula (1) can be produced for example by the following methods.

{Synthetic Method 1}

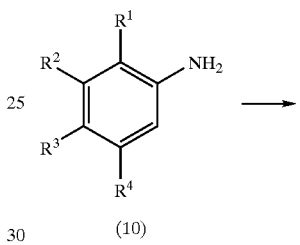

(10)

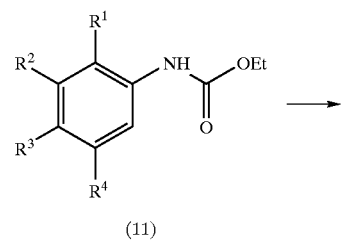

(11)

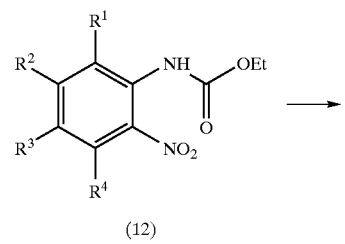

(12)

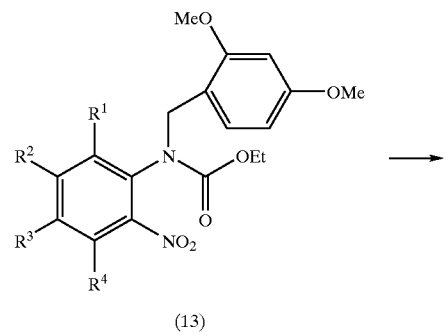

(13)

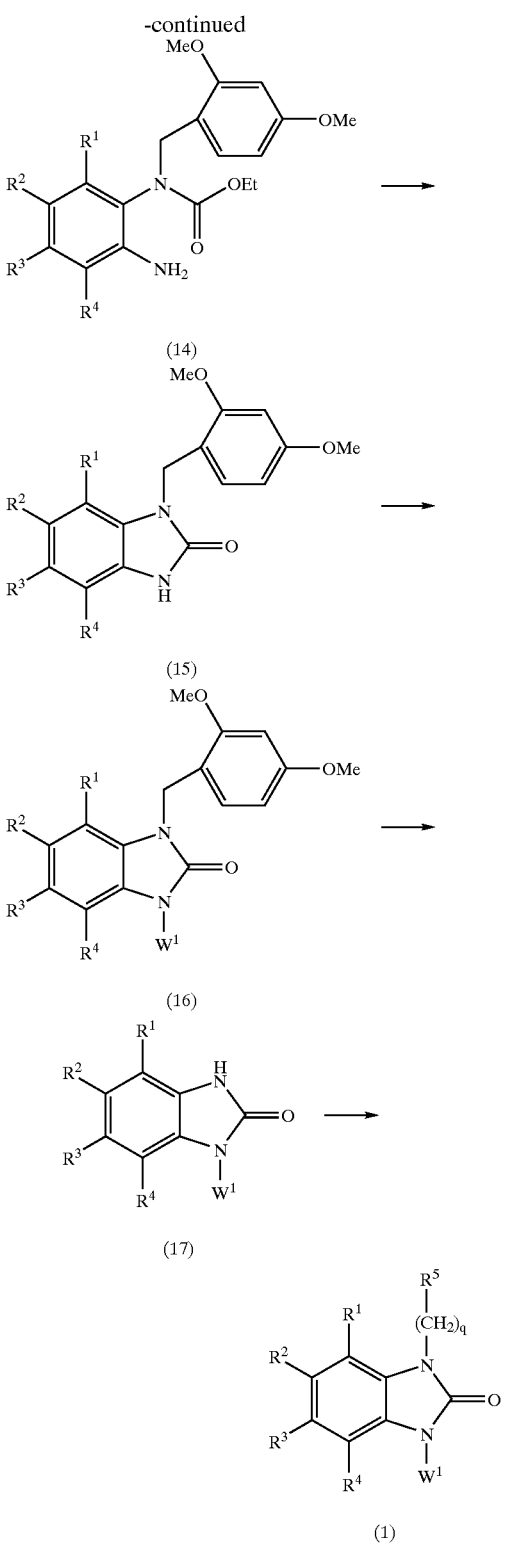

wherein $R^1$, $R^2$, $R^3$, $R^4$, $R^5$, $W^1$, and q are the same as those described in claim 1.

The compound represented by the formula (11) can be prepared by reaction of compound (10) with ethyl chloroformate in the presence of a base with or without an inert solvent. The base includes, for example, an organic bases such as pyridine, 4-N,N,-dimethylaminopyridine, and the like. The inert solvent includes halogenated solvents such as dichloromethane, 1,2-dichloroethane, and the like, ethereal solvents such as tetrahydrofuran and the like, and dimethylformamide and the like. The reaction temperature may be selected in the range of about −10° C. to room temperature.

The compound represented by the formula (12) can be prepared by reaction of compound (11) and conc. nitric acid in the presence of a catalyst in an inert solvent. The catalyst includes, for example, an acid such as conc. sulfuric acid and the like. The inert solvent includes, for example, acetic anhydride and the like. The reaction temperature may be selected in the range of about −10° C. to room temperature.

The compound represented by the formula (13) can be prepared by reaction of compound (12) with 2,4-dimethoxybenzyl alcohol in the presence of triphenylphosphine and diethyl azodicarboxylate in an inert solvent. The inert solvent includes halogenated solvents such as dichloromethane, 1,2-dichloroethane, and the like, ethereal solvents such as tetrahydrofuran and the like, dimethylformamide and the like. The reaction temperature may be selected in the range of about 0° C. to room temperature.

The compound represented by the formula (14) can be prepared by reaction of compound (13) in the presence of a reducing agent in an inert solvent. The reducing agent includes, for example, titanium trichloride and the like. The inert solvent includes, for example, alcoholic solvents such as methanol, ethanol etc., and the like. The reaction temperature may be selected in the range of about −10° C. to room temperature.

The compound represented by the formula (15) can be prepared by reaction compound (14) in the presence of a base in an inert solvent. The base includes, for example, alkaline metal hydrides such as sodium hydride etc., and the like. The inert solvent includes, for example, alcoholic solvents such as methanol, ethanol etc., and the like. The reaction temperature may be selected in the range of room temperature to around the boiling temperature of the solvent.

The compound represented by the formula (16) can be prepared by reaction of compound (15) with $W^1$-X in the presence of a base in an inert solvent wherein X means a leaving group such as halogen atoms including chlorine, bromine, iodine etc., and the like. The base includes, for example, alkaline metal hydrides such as sodium hydride etc., and the like, organic bases such as pyridine, 4-N,N,-dimethylaminopyridine and the like, and the combination of these. The inert solvent includes, for example, ethereal solvents such as tetrahydrofuran and the like, dimethylformamide and the like. The reaction temperature may be selected in the range of about −10° C. to 150° C.

The compound represented by the formula (17) can be prepared by reaction of compound (16) with ceric ammonium nitrate (IV) in an inert solvent. The inert solvent includes, for example, water, acetonitrile and the like, and the mixture of these solvents and the like. The reaction temperature may be selected in the range of about 0° C. to room temperature.

The compound represented by the formula (1) can be prepared by reaction of compound (17) with $R^5$—$(CH_2)_q$—X in the presence of a base in an inert solvent, wherein X means a leaving group such as halogen atoms including chlorine, bromine, iodine etc., and the like. The base includes, for example, alkaline metal carbonates such as potassium carbonate, sodium carbonate and the like, and organic bases such as pyridine, 4-N,N,-dimethylaminopyridine and the like. The inert solvent includes, for example, ethereal solvents such as tetrahydrofuran and the like, and dimethylformamide and the like. The reaction temperature may be selected in the range of room temperature to around the boiling temperature of the solvent.

{Synthetic Method 2}

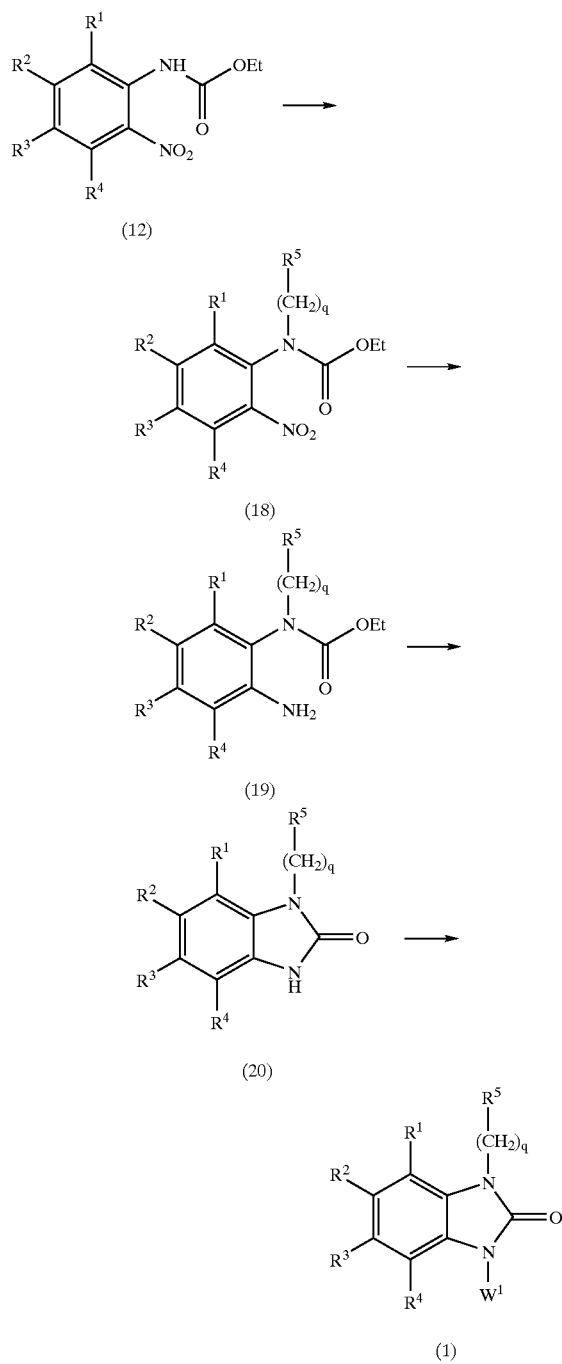

wherein $R^1$, $R^2$, $R^3$, $R^4$, $R^5$, $W^1$, and q are the same as those described in claim 1.

The compound represented by the formula (18) can be prepared by reaction of compound (12) with $R^5$—$(CH_2)_q$—X in the presence of a base in an inert solvent, wherein X means a leaving group such as halogen atoms including chlorine, bromine, iodine etc., and the like. The base includes, for example, alkaline metal carbonates such as potassium carbonate, sodium carbonate and the like, and organic bases such as pyridine, 4-N,N,-dimethylaminopyridine and the like. The inert solvent includes, for example, ethereal solvents such as tetrahydrofuran and the like, dimethylformamide and the like. The reaction temperature may be selected in the range of room temperature to around the boiling temperature of the solvent.

The compound represented by the formula (19) can be prepared by reaction of compound (18) with a reducing agent in an inert solvent. The reducing agent includes, for example, titanium trichloride, combination of nickel chloride (II) and sodium borohydride, and the like. The inert solvent includes, for example, alcoholic solvents such as methanol, ethanol etc., and the like. The reaction temperature is selected from the range of from about −10° C. to room temperature.

The compound represented by the formula (19) can also be obtained by catalytic hydrogenation of compound (18) in the presence of a catalyst in an inert solvent. The catalyst includes noble metal catalysts such as palladium charcoal, platinum oxide etc., and the like. The inert solvent includes, for example, alcoholic solvents such as methanol, ethanol etc., and the like. The pressure of catalytic hydrogenation may be, for example, at around an atmospheric pressure. The reaction temperature may be selected in the range of room temperature to about 40° C.

The compound represented by the formula (20) can be obtained by reacting compound (19) in the presence of a base in an inert solvent. The base includes, for example, alkaline metal hydrides such as sodium hydride etc., and the like. The inert solvent includes, for example, alcoholic solvents such as methanol, ethanol etc., and the like. The reaction temperature may be selected in the range of room temperature to around the boiling temperature of the solvent.

The compound represented by the formula (1) can be prepared by reaction of compound (20) with $W^1$-X in the presence of a base in an inert solvent wherein X means a leaving group such as halogen atoms including chlorine, bromine, iodine etc., and the like. The base includes, for example, alkaline metal hydrides such as sodium hydride etc., and the like, organic bases such as pyridine, 4-N,N,-dimethylaminopyridine and the like, and the combination of these. The inert solvent includes, for example, ethereal solvents such as tetrahydrofuran and the like, dimethylformamide and the like. The reaction temperature may be selected in the range of about −10° C. to 150° C.

{synthetic method 3}

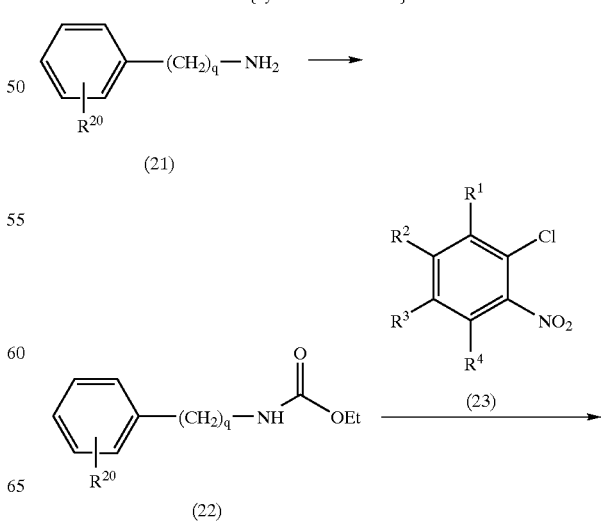

-continued

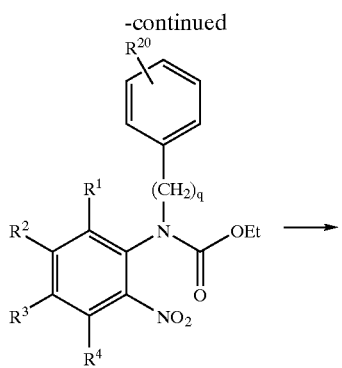

(24)

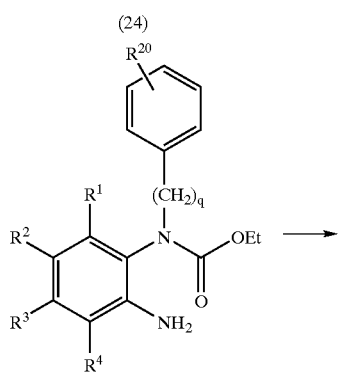

(25)

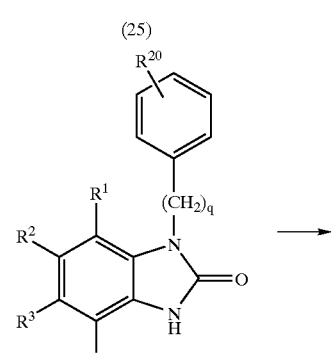

(26)

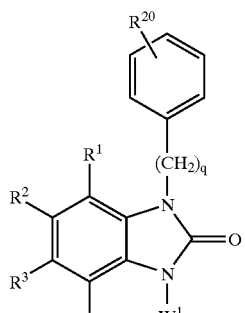

(1')

wherein $R^1$, $R^2$, $R^3$, $R^4$, $R^5$, $W^1$, and q are the same as those described in claim 1. $R^{20}$ includes hydrogen atom; halogen atom which includes, for example, fluorine, chlorine, bromine and the like; $C_{1-3}$ alkyl which includes, for example, methyl, ethyl, propyl, and the like; $C_{1-3}$ substituted alkyl whose substituents include, for example, halogen atom which includes, for example, fluorine, chlorine, bromine and the like, amino, hydroxy, and the like; $C_{1-3}$ alkoxy which includes, for example, methoxy, ethoxy, propoxy, and the like; or substituted phenyl whose substituents include, for example, halogen atom which includes, for example, fluorine, chlorine, bromine and the like, $C_{1-3}$ alkyl which includes, for example, methyl, ethyl, propyl, and the like, and $C_{1-3}$ alkoxy which includes, for example, methoxy, ethoxy, propoxy, and the like. The number of the substituents $R^{20}$ may be one or more.

The compound represented by the formula (22) can be prepared by reaction of compound (21) with ethyl chloroformate in the presence of a base with or without an inert solvent. The base includes, for example, an organic bases such as pyridine, 4-N,N,-dimethylaminopyridine, and the like. The inert solvent includes, for example, halogenated solvents such as dichloromethane, 1,2-dichloroethane, and the like, ethereal solvents such as tetrahydrofuran and the like, dimethylformamide and the like. The reaction temperature may be selected in the range of about −10° C. to room temperature.

The compound represented by the formula (24) can be prepared by reaction of compound (22) with compound (23) in the presence of a base in an inert solvent. The base includes, for example, alkaline metal hydrides such as sodium hydride etc., and the like. The inert solvent includes, for example, tetrahydrofuran, solvents having high boiling points such as diglyme, dimethylformamide etc., and the like. The reaction temperature may be selected in the range of room temperature to around the boiling temperature of the solvent.

The compound represented by the formula (25) can be prepared by reaction of compound (24) in the presence of a reducing agent in an inert solvent. The reducing agent includes, for example, titanium trichloride, combination of nickel chloride (II) and sodium borohydride, and the like. The inert solvent includes, for example, alcoholic solvents such as methanol, ethanol etc., and the like. The reaction temperature may be selected in the range of about −10° C. to room temperature.

In addition, the compound represented by the formula (25) can also be obtained by catalytic hydrogenation of compound (24) in the presence of a catalyst in an inert solvent. The catalyst includes noble metal catalysts such as palladium charcoal, platinum oxide etc., and the like. The inert solvent includes, for example, estereal solvents such as ethyl acetate and the like, alcoholic solvents such as methanol, ethanol etc., and the like. The pressure of catalytic hydrogenation may be, for example, at around an atmospheric pressure. The reaction temperature may be selected in the range of room temperature to about 40° C.

The compound represented by the formula (26) can be prepared by reaction compound (25) in the presence of a base in an inert solvent. The base includes, for example, alkaline metal hydrides such as sodium hydride etc., and the like. The inert solvent includes, for example, alcoholic solvents such as methanol, ethanol etc., and the like. The reaction temperature may be selected in the range of room temperature to around the boiling temperature of the solvent.

The compound represented by the formula (1') can be prepared by reaction of compound (26) with $W^1$-X in the presence of a base in an inert solvent wherein X means a leaving group such as halogen atoms including chlorine, bromine, iodine etc., and the like. The base includes, for example, alkaline metal hydrides such as sodium hydride etc., and the like, organic bases such as pyridine, 4-N,N,-dimethylaminopyridine and the like, and the combination of these. The inert solvent includes, for example, ethereal solvents such as tetrahydrofuran and the like, dimethylformamide and the like. The reaction temperature may be selected in the range of about −10° C. to 150° C.

Compounds produced according to the above methods can be isolated and purified by a conventional method such as recrystallization, column chromatography, HPLC and the like.

In the above reactions, functional groups may be protected if needed. Examples of the protective groups include the known protective groups (e.g., Protective Groups in Organic Synthesis, T. W. Greene, A Wiley-Interscience Publication (1981)) and the like.

When the benzimidazolidinone derivatives of the formula (1) are produced according to the above-mentioned production method, they may be obtained as a mixture of isomers. In this case, each isomer of the benzimidazolidinone derivatives of the formula (1) or a production intermediate can be isolated and purified by a suitable purification method such as silica gel column chromatography and the like.

The benzimidazolidinone derivatives of the formula (1) of the present invention may have asymmetries or substituents with asymmetric carbon atoms. In such compounds, optical isomers and geometrical isomers are present. The benzimidazolidinone derivatives of the formula (1) of the present invention include a mixture of such isomers and an isolated one. As a method for obtaining such pure optical isomers may be, for example, optical resolution.

As a method for optical resolution, the benzimidazolidinone derivatives of the formula (1) of the present invention or an intermediate thereof may form a salt with an optically active acid (e.g., monocarboxylic acids such as mandelic acid, N-benzyloxyalanine, lactic acid, etc., dicarboxylic acids such as tartaric acid, O-diisopropylidene tartaric acid, malic acid, etc., and sulfonic acids such as camphor sulfonic acid, bromocamphorsulfonic acid, etc.) in an inert solvent (e.g., alcoholic solvent such as methanol, ethanol, 2-propanol, etc., ethereal solvent such as diethyl ether, etc., estereal solvent such as ethyl acetate, etc., aromatic hydrocarbon solvent such as toluene, etc., acetonitrile etc., or a mixture thereof).

When the benzimidazolidinone derivatives of the formula (1) of the present invention or an intermediate thereof has an acidic substituent such as carboxyl group, etc., a salt may be formed with an optically active amine (e.g., organic amines such as α-phenethylamine, quinine, quinidine, cinchonidine, cinchonine, strychnine, etc.).

The temperature for forming a salt is in the range of from room temperature to the boiling point of the solvent. In order to improve the optical purity, it is desirable to once raise the temperature to around the boiling point of the solvent, and before collecting the precipitated salts by filtration, the reaction mixture is cooled as necessary to improve the yield. The optically active acid or amine is used in an amount of about 0.5 to about 2.0 equivalents, preferably about one equivalent, relative to the substrate. If necessary, the resulting crystals are recrystallized from an inert solvent such as alcoholic solvents (e.g., methanol, ethanol, 2-propanol, etc.), ethereal solvents (e.g., diethyl ether, etc.), estereal solvents (e.g., ethyl acetate, etc.), aromatic hydrocarbon solvents (e.g., toluene, etc.), acetonitrile and the like, or a mixture of these solvents to give an optically active salt having a high purity. If necessary, the resulting salt is also treated with an acid or a base in a conventional manner to give a free form.

The benzimidazolidinone derivatives of the formula (1) can be converted to a salt by mixing with a pharmaceutically acceptable acid such as trifluoroacetic acid, hydrochloric acid, oxalic acid, methanesulfonic acid and the like in a solvent such as water, methanol, ethanol, acetone and the like.

The benzimidazolidinone derivatives of the formula (1) of the present invention and pharmaceutically acceptable salts thereof can promote release of endogenous growth hormone, so that they have effects and utilities similar to those of the growth hormone. Specific use of the benzimidazolidinone derivatives of the formula (1) of the present invention and pharmaceutically acceptable salts thereof are, for example, as follows:

stimulation of growth hormone release in the elderly; treating growth hormone deficient adults; prevention of catabolic side effects of glucocorticoids; treatment of osteoporosis; activation of the immune system; acceleration of wound healing; accelerating bone fracture repair; treatment of growth retardation; treating acute or chronic renal failure or renal insufficiency; treatment of physiological short stature including growth hormone deficient children; treatment of short stature associated with chronic illness; treatment of obesity and growth retardation associated with obesity; treating growth retardation associated with the Prader-Willi syndrome and Turner's syndrome; accelerating the recovery and reducing hospitalization of burn patients; accelerating the recovery and reducing hospitalization following major surgery such as gastrointestinal surgery; treatment of intrauterine growth retardation, skeletal dysplasia, hypercortisolism and Cushing's syndrome; replacement of growth hormone in stressed patients; treatment of osteochondrodysplasias, Noonan's syndrome, sleep disorder, Alzheimer's disease, and delayed wound healing; treatment of pulmonary dysfunction and ventilator dependency; treatment of attenuation of protein catabolic responses after major surgery and malabsorption syndromes; reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction; adjuvant treatment to prevent and treat gastric and duodenal ulcers; stimulation of thyroid development; prevention of the age-related decline of thyroid function; adjunctive therapy for patients on chronic hemodialysis; treatment of immunosuppressed patients; treatment of enhanced antibody response following vaccination; improvement in muscle strength and mobility in the frail elderly; maintenance of skin thickness, metabolic homeostasis and renal homeostasis in the frail elderly; stimulation of osteoblasts, bone remodelling and cartilage growth in the frail elderly; treatment of peripheral neurological diseases and drug induced neuropathy, Guillian-Barre Syndrome, amyotrophic lateral sclerosis, multiple sclerosis, cerebrovascular disorders and demyelinating diseases; activation of the immune system in companion animals; treatment of disorders of aging in companion animals; growth promotion in livestock; stimulation of wool growth in sheep; ulcerative colitis; and the like.

Therefore, benzimidazolidinone derivatives of the present invention and pharmaceutically acceptable salts thereof, which promote release of endogenous growth hormone, are preferably applicable to the above uses as is the growth hormone.

The benzimidazolidinone derivatives of the formula (1) of the present invention or the pharmaceutically acceptable salt thereof may be applicable to not only humans but also to, for example, mammals such as mice, rats, dogs, cows, horses, goats, sheep, rabbits, pigs and the like.

The benzimidazolidinone derivatives of the formula (1) of the present invention or the pharmaceutically acceptable salt thereof can be administered either orally or parenterally.

When administered orally, it can be administered in a conventionally used administration form. They can be administered parenterally in the form of an agent for local administration, injections, percutaneous formulations, intranasal formulations, etc. Agents for oral or rectal administration include, for example, capsules, tablets, pills, powders, cachets, suppositories, liquids, etc. The injection includes, for example, aseptic solutions or suspensions, etc. The agent for local administration includes, for example, creams, ointments, lotions, percutaneous agents (e.g., conventional patches, matrixes) and the like.

The above-mentioned dosage forms are produced as pharmaceutical preparation together with pharmaceutically acceptable excipients and additives according to a conventional method. The pharmaceutically acceptable excipient or additive includes carriers, binders, flavors, buffers, thickening agents, coloring agents, stabilizers, emulsifiers, dispersing agents, suspending agents, preservatives, etc.

The pharmaceutically acceptable carrier includes, for example, magnesium carbonate, magnesium stearate, talc, sugar, lactose, pectin, dextrin, starch, gelatin, tragacanth, methyl cellulose, sodium carboxymethyl cellulose, low-melting wax, cacao butter, etc. The benzimidazolidinone derivative of the formula (1) of the present invention or a pharmaceutically acceptable salt thereof is enclosed in capsules after mixing with a pharmaceutically acceptable excipient, or without an excipient. Cachets can be produced according to a similar method.

Liquid preparations for injection include, for example, solutions, suspensions, emulsions, etc. For example, aqueous solution, water-propylene glycol solution, etc. can be mentioned. Liquid preparation can be also produced in the form of a solution of polyethylene glycol or/and propylene glycol which may contain water. Liquid preparation suitable for oral administration may be prepared by adding the benzimidazolidinone derivative of the present invention or a pharmaceutically acceptable salt thereof into water, and adding thereto coloring agents, flavors, stabilizers, sweetening agents, solubilizers, thickening agents and the like, if necessary. In addition, liquid preparation suitable for oral administration can be also produced by adding the benzimidazolidinone derivative of the formula (1) of the present invention or a pharmaceutically acceptable salt thereof into water together with a dispersing agent and further making the mixture viscous. The thickening agent includes, for example, pharmaceutically acceptable natural or synthesized gum, resin, methyl cellulose, sodium carboxymethyl cellulose, or a known suspending agent, etc.

The preparation for local administration includes the above-mentioned liquid preparations, and creams, aerosols, sprays, powders, lotions, ointments, etc. The above-mentioned preparation for local administration is prepared by mixing the benzimidazolidinone derivative of the formula (1) of the present invention or a pharmaceutically acceptable salt thereof with a conventionally used pharmaceutically acceptable diluent or carrier. The ointments and creams are obtained by, for example, adding a thickening agent and/or gelatinizing agent to an aqueous or oily base, and preparating. Said base includes, for example, water, liquid paraffin, vegetable oil (peanut oil, caster oil, etc.), etc. The thickening agent includes, for example, soft paraffin, aluminum stearate, cetostearyl alcohol, propylene glycol, polyethylene glycol, lanoline, hydrogenated lanoline, bees wax, etc.

The lotion may be obtained by adding one or more pharmaceutically acceptable stabilizers, suspending agents, emulsifiers, dispersing agents, thickening agents, coloring agents, flavors, etc. to an aqueous or oily base.

Powders are formulated into preparation with a pharmaceutically acceptable base for powders. The base includes, for example, talc, lactose, starch, etc. Drops are formulated with an aqueous or non-aqueous base and one or more pharmaceutically acceptable dispersing agents, suspending agents, solubilizers, etc.

The preparation for local administration may contain, where necessary, antiseptic agents or bacterial growth inhibitors such as methyl hydroxybenzoate, propyl hydroxybenzoate, chlorocresol, benzalkonium chloride, etc.

A pharmaceutical preparation in the form of a liquid spray, powder or drop, which contains the benzimidazolidinone derivative of the formula (1) of the present invention or a pharmaceutically acceptable salt thereof as an active ingredient, can be administered nasally.

The dosage and the frequency of administration may vary according to the conditions, ages, weights, the administration form, etc. For oral administration, generally, a dose of about 1 to about 500 mg per day, preferably about 5 to about 100 mg, per day is given to an adult once or in several portions. For administration as an injection, a dose of about 0.1 to about 300 mg, preferably about 1 to about 100 mg, is given once or in several portions.

EXAMPLES

The present invention will be described in detail below, referring to reference examples and examples, which are not limitative of the present invention. The HPLC condition used for the purification of the example compounds are as follows.
Condition 1
column: YMC-ODS A-211 (YMC Co., Ltd.)
liquid A: $H_2O$/0.1% trifluoroacetic acid
liquid B: acetonitrile/0.1% trifluoroacetic acid
B%: 30%→30 min→90%
wavelength: 254 nm
flow rate: 1.0 ml/min
Condition 2
column: YMC-ODS A-211 (YMC Co., Ltd.)
liquid A: $H_2O$/0.1% trifluoroacetic acid
liquid B: acetonitrile/0.1% trifluoroacetic acid
B%: 10%→40 min→90%
wavelength: 254 nm
flow rate: 1.0 ml/min Example 1

Synthesis of 1-(2-chlorophenyl)-3-[2-(diethylamino)ethyl]-2-oxo-7-(trifluoromethyl)-2,3-dihydro-1H-benzimidazole-5-carboxamide trifluoroacetate Example 1-1

Synthesis of ethyl 2-chlorophenylcarbamate

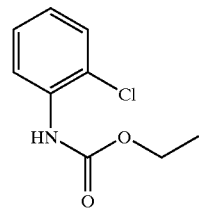

2-Chloroaniline (1.4463 g) was dissolved in pyridine (10 ml), and to the solution was added dropwise ethyl chloroformate (1.30 ml) under ice-cooling. After the mixture was stirred for 1 hour, 1N hydrochloric acid was added and the mixture was extracted with ethyl acetate. The organic layer was washed with 1N hydrochloric acid, and then saturated brine, dried over anhydrous magnesium sulfate, and concentrated in vacuo to give the title compound (2.2203 g, 98%).

¹H-NMR (CDCl₃, 300 MHz) δ 1.33 (3H, t, J=7.1 Hz), 4.24 (2H, q, J=7.0 Hz), 6.97 (1H, dt, J=7.7, 1.4 Hz), 7.14 (1H, brs), 7.25 (1H, dt, J=7.9, 1.5 Hz), 7.33 (H, dd, J=8.1, 1.5 Hz), 8.16 (1H, brd, J=8.1 Hz).

Example 1-2

Synthesis of ethyl 2-chlorophenyl[2,4-dinitro-6-(trifluoromethyl)phenyl]carbamate

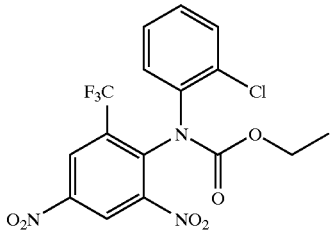

Ethyl 2-chlorophenylcarbamate (62.6 mg) was dissolved in diglyme (1 ml), and to the solution were added sodium hydride (12.6 mg) and 2-chloro-3,5-dinitrobenzotrifluoride (77.1 mg). The reaction mixture was stirred at room temperature for 1 hour. To the reaction mixture was added 1N hydrochloric acid, and the mixture was extracted with ethyl acetate. The organic layer was washed with 1N hydrochloric acid, saturated aqueous sodium bicarbonate solution, and then saturated brine, dried over anhydrous magnesium sulfate, and concentrated in vacuo. The resultant residue was purified by preparative TLC (2 mm, 20×20 cm, hexane:ethyl acetate=3:1) to give the title compound (114.8 mg, 93%).

¹H-NMR (CDCl₃, 300 MHz) δ 1.29–1.21 (3H, m), 4.32–4.23 (2H, m), 7.28–7.03 (3H, m), 7.51–7.35 (1H, m), 8.80 (1H, d, J=2.8 Hz), 8.96 (1H, brd, J=14.1 Hz).

Example 1-3

Synthesis of ethyl 2-chlorophenyl[2,4-diamino-6-(trifluoromethyl)phenyl]carbamate

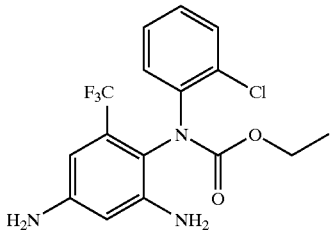

Ethyl 2-chlorophenyl[2,4-dinitro-6-(trifluoromethyl)phenyl]carbamate (0.645 g) was dissolved in ethyl acetate (100 ml), and to the solution was added 10% Pd—C (0.58 g). The reaction mixture was stirred under hydrogen atmosphere for 11 hours. The catalyst was filtered, and washed with ethyl acetate. The filtrate and washing were combined and concentrated in vacuo to give the title compound (0.543 g, 98%).

¹H-NMR (CDCl₃, 300 MHz) δ 1.23 (3H, t, J=7.0 Hz), 3.98 (4H, brs), 4.21 (2H, q, J=7.0 Hz), 6.13 (1H, d, J=2.4 Hz), 6.39 (1H, d, J=2.5 Hz), 7.23–7.10 (3H, m), 7.42 (1H, d, J=7.7 Hz).

Example 1-4

Synthesis of 5-amino-1-(2-chlorophenyl)-7-(trifluoromethyl)-1,3-dihydro-2H-benzimidazol-2-one

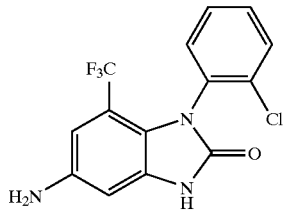

Ethyl 2-chlorophenyl[2,4-diamino-6-(trifluoromethyl)phenyl]carbamate (68.8 mg) was dissolved in ethanol (6 ml), and to the solution was added sodium hydride (14.7 mg). The reaction mixture was heated at reflux for 2 hours. After allowing to cool, to the reaction mixture was added saturated aqueous sodium bicarbonate solution, and the mixture was extracted 3 times with chloroform. The organic layer was washed with water, dried over anhydrous sodium sulfate, and concentrated in vacuo. The resultant residue was purified by preparative TLC (2 mm, 20×20 cm, CHCl₃:methanol=5:1) to give the title compound (46.2 mg).

Example 1-5

Synthesis of 1-(2-chlorophenyl)-2-oxo-7-(trifluoromethyl)-2,3-dihydro-1H-benzimidazole-5-carbonitrile

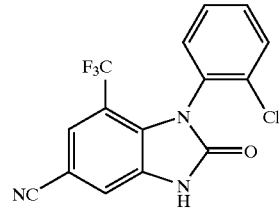

5-Amino-1-(2-chlorophenyl)-7-(trifluoromethyl)-1,3-dihydro-2H-benzimidazole-2-one (46.2 mg) was dissolved in dimethyl sulfoxide (1 ml), and to the solution was added CuCN (16.4 mg). The mixture was heated at 55° C. At the same temperature, a solution of t-butyl nitrite (43.6 mg) in dimethyl sulfoxide (0.5 ml) was added dropwise during about 1.5 hours. After the addition was completed, the mixture was stirred at about 60° C. for 1 hour. After allowing to cool, to the reaction mixture was added water, and the mixture was extracted 2 times with ethyl acetate. The organic layer was washed with saturated brine, dried over anhydrous magnesium sulfate, and concentrated in vacuo. The resultant residue was purified by silica gel column (20 g, CHCl₃-methanol=20:1) to give the title compound (17.6 mg).

Example 1-6

Synthesis of 1-(2-chlorophenyl)-3-[2-(diethylamino)ethyl]-2-oxo-7-(trifluoromethyl)-2,3-dihydro-1H-benzimidazole-5-carboxamide trifluoroacetate

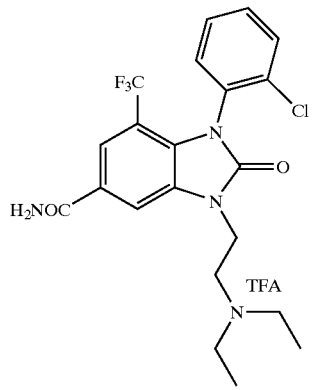

1-(2-Chlorophenyl)-2-oxo-7-(trifluoromethyl)-2,3-dihydro-1H-benzimidazole-5-carbonitrile (17.6 mg) was dissolved in N,N-dimethylformamide (1.5 ml), and to the solution was added sodium hydride (2.7 mg). The mixture was stirred at room temperature for 20 minutes. A solution of 2-chlorotriethylamine hydrochloride (11.7 mg) in N,N-dimethylformamide (2 ml) and triethylamine (0.011 ml) were added, and the mixture was stirred at 60–70° C. for 1 hour. After allowing to cool, to the reaction mixture was added saturated aqueous sodium bicarbonate solution, and the mixture was extracted with ethyl acetate. The organic layer was washed with water, dried over anhydrous sodium sulfate, and concentrated in vacuo. The resultant residue was dissolved in 2-methyl-2-propanol (1 ml) and heated at 50° C. To the solution was added powdered potassium hydroxide (73.1 mg), and the mixture was stirred for 1 hour. After allowing to cool, to the reaction mixture was added water, and the mixture was extracted 4 times with ethyl acetate. The organic layer was washed with saturated brine, dried over anhydrous sodium sulfate, and concentrated in vacuo. The resultant residue was purified by HPLC using condition 1 to give the title compound (6.2 mg, 6%).

$^1$H-NMR (DMSO-$d_6$, 300 MHz) δ 1.20 (6H, t, J=7.1 Hz), 3.65–3.15 (6H, m), 4.37 (2H, t, J=6.6 Hz), 7.72–7.51 (5H, m), 7.98 (1H, s), 8.19 (1H, brs), 8.21 (1H, s), 9.64 (1H, brs). HPLC retention time: 13.8 min (condition 1).

Example 2

Synthesis of 1-(2-chlorobenzyl)-3-[2-(diethylamino)ethyl]-2-oxo-7-(trifluoromethyl)-2,3-dihydro-1H-benzimidazole-5-carboxamide trifluoroacetate and 1-benzyl-3-[2-(diethylamino)ethyl]-2-oxo-7-(trifluoromethyl)-2,3-dihydro-1H-benzimidazole-5-carboxamide trifluoroacetate

Example 2-1

Synthesis of ethyl 2-chlorobenzylcarbamate

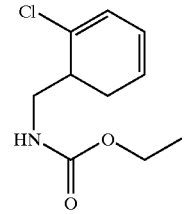

2-Chlorobenzylamine (1.7734 g) was dissolved in pyridine (10 ml), and to the solution was added dropwise ethyl chloroformate (1.437 ml) during 20 minutes under ice-cooling. After the mixture was stirred for 40 minutes, 1N hydrochloric acid was added and the mixture was extracted with ethyl acetate. The organic layer was washed with 1N hydrochloric acid, saturated aqueous sodium bicarbonate solution, and then saturated brine, dried over anhydrous magnesium sulfate, and concentrated in vacuo to give the title compound (2.715 g, quantitative yield).

$^1$H-NMR (CDCl$_3$, 300 MHz) δ 1.24 (3H, t, J=7.1 Hz), 4.12 (2H, q, J=7.0 Hz), 4.43 (2H, d, J=6.4 Hz), 5.24 (1H, brs), 7.24–7.17 (2H, m), 7.40–7.31 (2H, m).

Example 2-2

Synthesis of ethyl 2-chlorobenzyl[2,4-dinitro-6-(trifluoromethyl)phenyl]carbamate

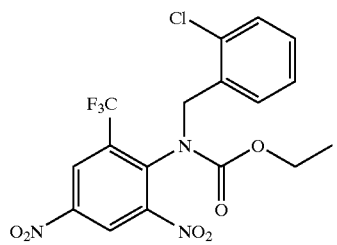

Ethyl 2-chlorobenzylcarbamate (809.9 mg) and 2-chloro-3,5-dinitrobenzotrifluoride (932.3 mg) were dissolved in tetrahydrofuran (20 ml), and to the solution was added sodium hydride (151.6 mg) under ice-cooling. The reaction mixture was heated at reflux for 5 hours. After allowing to cool, to the reaction mixture was added 1N hydrochloric acid (200 ml), and the mixture was extracted with ethyl acetate. The organic layer was washed with saturated aqueous sodium bicarbonate solution, and then saturated brine, dried over anhydrous magnesium sulfate, and concentrated in vacuo. The resultant residue was purified by silica gel column (100 g, hexane:ethyl acetate=5:1) to give the title compound (0.286 g, 19%).

¹H-NMR (CDCl₃, 300 MHz) δ 1.14 (3H, t, J=7.0 Hz), 4.19 (2H, dq, J=7.1, 2.2 Hz), 4.69 (1H, d, J=14.8 Hz), 5.30 (1H, d, J=14.8 Hz), 7.30–7.17 (3H, m), 7.60–7.57 (1H, m), 8.83 (2H, s).

Example 2-3

Synthesis of ethyl 2-chlorobenzyl[2,4-diamino-6-(trifluoromethyl)phenyl]carbamate

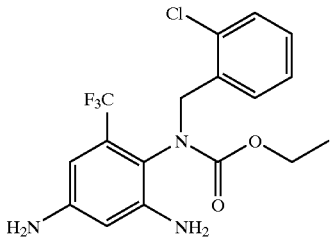

Ethyl 2-chlorobenzyl[2,4-dinitro-6-(trifluoromethyl)phenyl]carbamate (103.8 mg) was dissolved in ethyl acetate (20 ml), and to the solution was added 10% Pd—C (105.3 mg). The reaction mixture was stirred under hydrogen atmosphere for 7 hours. The catalyst was filtered, and washed with ethyl acetate. The filtrate was concentrated in vacuo to give the title compound (85.6 mg).

Example 2-4

Synthesis of 5-amino-1-(2-chlorobenzyl)-7-(trifluoromethyl)-1,3-dihydro-2H-benzimidazol-2-one

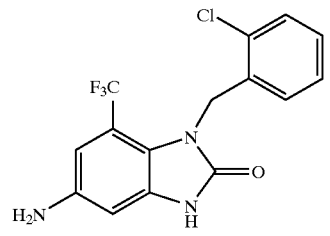

Ethyl 2-chlorobenzyl[2,4-diamino-6-(trifluoromethyl)phenyl]carbamate (85.6 mg) was dissolved in ethanol (10 ml), and to the solution was added sodium hydride (17.7 mg). The reaction mixture was heated at reflux for 24 hours. After allowing to cool, to the reaction mixture was added saturated aqueous sodium bicarbonate solution, and the mixture was extracted 4 times with chloroform. The organic layer was washed with saturated brine, dried over anhydrous sodium sulfate, and concentrated in vacuo. The resultant residue was purified by preparative TLC (2 mm, 20×20 cm, CHCl₃-methanol=5:1) to give the title compound (46.0 mg).

Example 2-5

Synthesis of 1-(2-chlorobenzyl)-3-[2-(diethylamino)ethyl]-2-oxo-7-(trifluoromethyl)-2,3-dihydro-1H-benzimidazole-5-carboxamide trifluoroacetate and 1-benzyl-3-[2-(diethylamino)ethyl]-2-oxo-7-(trifluoromethyl)-2,3-dihydro-1H-benzimidazole-5-carboxamide trifluoroacetate

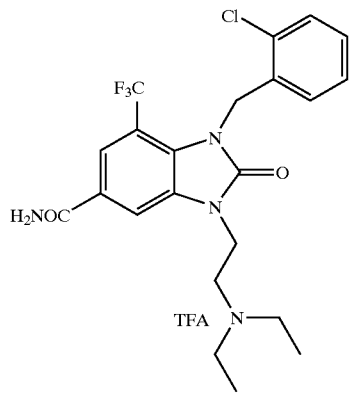

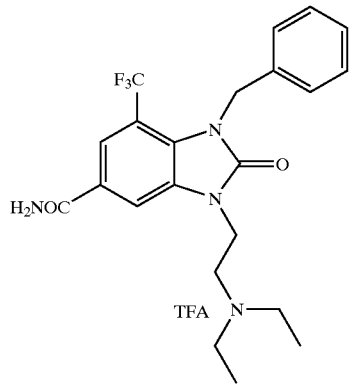

5-Amino-1-(2-chlorobenzyl)-7-(trifluoromethyl)-1,3-dihydro-2H-benzimidazol-2-one (46.0 mg) was dissolved in dimethyl sulfoxide (1 ml), and to the solution was added CuCN (15.7 mg). The mixture was heated at 55° C. At the same temperature, a solution of t-butyl nitrite (41.6 mg) in dimethyl sulfoxide (0.5 ml) was added dropwise during 2 hours. After the addition was completed, the mixture was stirred at 60° C. for 1 hour. After allowing to cool, to the reaction mixture was added saturated brine, and the mixture was extracted 2 times with ethyl acetate. The organic layer was washed with saturated brine, dried over anhydrous magnesium sulfate, and concentrated in vacuo. The resultant residue was dissolved in N,N-dimethylformamide (3 ml), and to the solution was added sodium hydride (7 mg). The mixture was stirred at room temperature for 10 minutes. A solution of 2-chlorotriethylamine hydrochloride (30.1 mg) in N,N-dimethylformamide (2 ml) and triethylamine (0.028 ml) were added, and the mixture was stirred at 60–70° C. for 1 hour. After allowing to cool, to the reaction mixture was added saturated aqueous sodium bicarbonate solution, and the mixture was extracted with ethyl acetate. The organic layer was washed with saturated brine, dried over anhydrous sodium sulfate, and concentrated in vacuo. The resultant residue was dissolved in 2-methyl-2-propanol (3 ml) and heated at 50° C. To the solution was added powdered potassium hydroxide (189 mg), and the mixture was stirred for 1 hour. After allowing to cool, to the reaction mixture was added saturated aqueous sodium bicarbonate solution, and the mixture was extracted with ethyl acetate. The organic layer was washed with saturated brine, dried over anhydrous sodium sulfate, and concentrated in vacuo. The resultant residue was purified by HPLC using condition 1 to give 1-(2-chlorobenzyl)-3-[2-(diethylamino)ethyl]-2-oxo-7-(trifluoromethyl)-2,3-dihydro-1H-benzimidazole-5-carboxamide trifluoroacetate (3.7 mg, 5%) and 1-benzyl-3-[2-(diethylamino)ethyl]-2-oxo-7-(trifluoromethyl)-2,3-dihydro-1H-benzimidazole-5-carboxamide trifluoroacetate (2.1 mg, 3%).

1-(2-Chlorobenzyl)-3-[2-(diethylamino)ethyl]-2-oxo-7-(trifluoromethyl)-2,3-dihydro-1H-benzimidazole-5-carboxamide trifluoroacetate.

$^1$H-NMR (DMSO-$d_6$, 300 MHz) δ 1.10 (6H, brs), 3.80–2.90 (6H, m), 4.40–4.10 (2H, m), 5.22 (2H, s), 6.78 (1H, d, J=7.3 Hz), 7.19 (1H, t, J=7.3 Hz), 7.30 (1H, t, J=7.3 Hz), 7.64–7.50 (3H, m), 7.98 (1H, s), 8.19 (1H, brs), 8.23 (1H, s). HPLC retention time: 17.6 min. (condition 1).

1-Benzyl-3-[2-(diethylamino)ethyl]-2-oxo-7-(trifluoromethyl)-2,3-dihydro-1H-benzimidazole-5-carboxamide trifluoroacetate.

$^1$H-NMR (DMSO-$d_6$, 300 MHz) δ 1.18 (6H, brs), 3.70–3.10 (6H, m), 4.50–4.30 (2H, m), 5.23 (2H, s), 7.15–7.00 (2H, m), 7.31–7.22 (3H, m), 7.59 (1H, brs), 7.99 (1H, s), 8.16 (1H, s), 8.22–8.12 (1H, m), 9.25 (1H, brs). HPLC retention time: 14.9 min. (condition 1).

Example 3

Synthesis of 1-(3-chlorobenzyl)-3-[2-(diethylamino)ethyl]-2-oxo-7-(trifluoromethyl)-2,3-dihydro-1H-benzimidazole-5-carboxamide trifluoroacetate Example 3-1

Synthesis of ethyl 3-chlorobenzylcarbamate

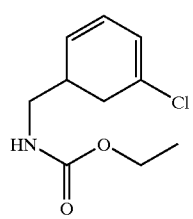

3-Chlorobenzylamine (0.8129 g) was dissolved in pyridine (5 ml), and to the solution was added dropwise ethyl chloroformate (0.659 ml) during 5 minutes under ice-cooling. After the mixture was stirred for 2 hours, 1N hydrochloric acid was added and the mixture was extracted with ethyl acetate. The organic layer was washed with 1N hydrochloric acid, saturated aqueous sodium bicarbonate solution, and then saturated brine, dried over anhydrous magnesium sulfate, and concentrated in vacuo to give the title compound (1.181 g, 96%).

$^1$H-NMR (CDCl$_3$, 300 MHz) δ 1.23 (3H, t, J=7.1 Hz), 4.13 (2H, q, J=7.1 Hz), 4.31 (2H, d, J=6.0 Hz), 5.25 (1H, brs), 7.30–7.13 (4H, m).

Example 3-2

Synthesis of ethyl 3-chlorobenzyl[2,4-dinitro-6-(trifluoromethyl)phenyl]carbamate

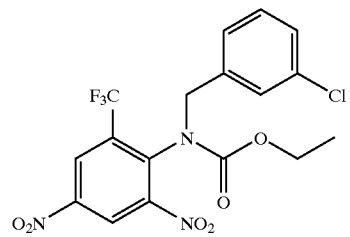

Ethyl 3-chlorobenzylcarbamate (720.3 mg) and 2-chloro-3,5-dinitrobenzotrifluoride (829.1 mg) were dissolved in tetrahydrofuran (20 ml), and to the solution was added sodium hydride (147.1 mg). The reaction mixture was heated at reflux for 1.5 hours. After allowing to cool, to the reaction mixture was added 1N hydrochloric acid, and the mixture was extracted with ethyl acetate. The organic layer was washed with saturated brine, dried over anhydrous magnesium sulfate, and concentrated in vacuo. The resultant residue was purified by silica gel column (75 g, hexane:ethyl acetate=10:1) to give the title compound (129.5 mg, 9%).

$^1$H-NMR (CDCl$_3$, 300 MHz) δ 1.14 (3H, t, J=7.0 Hz), 4.20 (2H, dq, J=7.1, 1.3 Hz), 4.26 (1H, d, J=14.6 Hz), 5.20 (1H, d, J=14.6 Hz), 7.30–7.02 (4H, m), 8.82 (2H, s).

Example 3-3

Synthesis of ethyl 3-chlorobenzyl[2,4-diamino-6-(trifluoromethyl)phenyl]carbamate

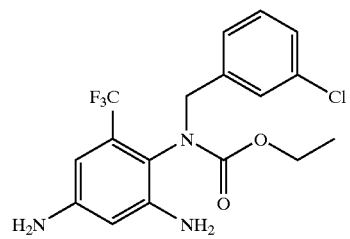

Ethyl 3-chlorobenzyl[2,4-dinitro-6-(trifluoromethyl)phenyl]carbamate (129.5 mg) was dissolved in ethyl acetate (20 ml), and to the solution was added 10% Pd—C (125.0 mg). The reaction mixture was stirred under hydrogen atmosphere for 7 hours. The catalyst was filtered, and washed with ethyl acetate. The filtrate was concentrated in vacuo to give the title compound (110.3 mg).

Example 3-4

Synthesis of 5-amino-1-(3-chlorobenzyl)-7-(trifluoromethyl)-1,3-dihydro-2H-benzimidazol-2-one

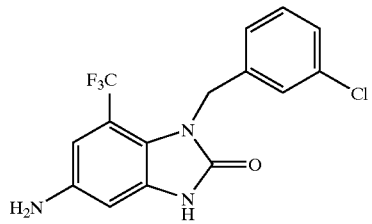

Ethyl 3-chlorobenzyl[2,4-diamino-6-(trifluoromethyl)phenyl]carbamate (110.3 mg) was dissolved in ethanol (10 ml), and to the solution was added sodium hydride (56.9 mg). The reaction mixture was heated at reflux for 5 hours. After allowing to cool, to the reaction mixture was added saturated aqueous sodium bicarbonate solution, and the mixture was extracted 4 times with chloroform. The organic layer was washed with saturated brine, dried over anhydrous sodium sulfate, and concentrated in vacuo. The resultant residue was purified by preparative TLC (2 mm, 20×20 cm, $CHCl_3$-methanol=5:1) to give the title compound (31.1 mg).

Example 3-5

Synthesis of 1-(3-chlorobenzyl)-3-[2-(diethylamino)ethyl]-2-oxo-7-(trifluoromethyl)-2,3-dihydro-1H-benzimidazole-5-carboxamide trifluoroacetate

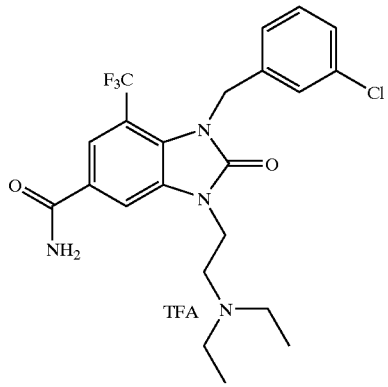

5-Amino-1-(3-chlorobenzyl)-7-(trifluoromethyl)-1,3-dihydro-2H-benzimidazol-2-one (31.1 mg) was dissolved in dimethyl sulfoxide (1 ml), and to the solution was added CuCN (10.6 mg). The mixture was heated at 55° C. At the same temperature, a solution of t-butyl nitrite (28.2 mg) in dimethyl sulfoxide (0.5 ml) was added dropwise during 1.5 hours. After the addition was completed, the mixture was stirred at 60° C. for 1 hour. After allowing to cool, to the reaction mixture was added saturated brine, and the mixture was extracted with ethyl acetate. The organic layer was washed with saturated brine, dried over anhydrous magnesium sulfate, and concentrated in vacuo. The resultant residue was dissolved in N,N-dimethylformamide (1 ml), and to the solution was added sodium hydride (4.7 mg). The mixture was stirred at room temperature for 5 minutes. A solution of 2-chlorotriethylamine hydrochloride (20.4 mg) in N,N-dimethylformamide (1 ml) and triethylamine (0.019 ml) were added, and the mixture was stirred at 60–70° C. for 1 hour. After allowing to cool, to the reaction mixture was added saturated aqueous sodium bicarbonate solution, and the mixture was extracted with ethyl acetate. The organic layer was washed with saturated brine, dried over anhydrous sodium sulfate, and concentrated in vacuo. The resultant residue was dissolved in 2-methyl-2-propanol (2 ml) and heated at 50° C. To the solution was added powdered potassium hydroxide (127.7 mg), and the mixture was stirred for 1 hour. After allowing to cool, to the reaction mixture was added saturated aqueous sodium bicarbonate solution, and the mixture was extracted with ethyl acetate. The organic layer was washed with saturated brine, dried over anhydrous sodium sulfate, and concentrated in vacuo. The resultant residue was purified by HPLC using condition 1 to give the title compound (0.6 mg, 1%).

$^1$H-NMR (DMSO-$d_6$, 300 MHz) δ 1.19 (6H, brs), 3.60–3.35 (6H, m), 4.50–4.20 (2H, m), 5.22 (2H, s), 7.15–7.00 (1H, m), 7.36–7.20 (3H, m), 7.63–7.55(1H, m), 7.99 (1H, s), 8.16 (2H, s), 9.18 (1H, brs). HPLC retention time: 17.5 min. (condition 1).

Example 4

Synthesis of 1-(4-chlorobenzyl)-3-[2-(diethylamino)ethyl]-2-oxo-7-(trifluoromethyl)-2,3-dihydro-1H-benzimidazole-5-carboxamide trifluoroacetate

Example 4-1

Synthesis of ethyl 4-chlorobenzylcarbamate

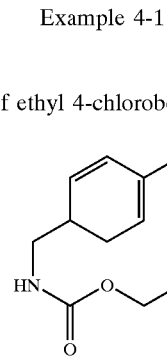

4-Chlorobenzylamine (1.0556 g) was dissolved in pyridine (5 ml), and to the solution was added dropwise ethyl chloroformate.(0.855 ml) during 5 minutes under ice-cooling. After the mixture was stirred for 3 hours, 1N hydrochloric acid was added and the mixture was extracted with ethyl acetate. The organic layer was washed with 1N hydrochloric acid, saturated aqueous sodium bicarbonate solution, and then saturated brine, dried over anhydrous magnesium sulfate, and concentrated in vacuo to give the title compound (1.562 g, 98%).

$^1$H-NMR (CDCl$_3$, 300 MHz) δ 1.24 (3H, t, J=7.1 Hz), 4.13 (2H, q, J=7.1 Hz), 4.30 (2H, d, J=6.0 Hz), 5.15 (1H, brs), 7.21 (2H, d, J=8.4 Hz), 7.29 (2H, d, J=8.5 Hz).

Example 4-2

Synthesis of ethyl 4-chlorobenzyl[2,4-dinitro-6-(trifluoromethyl)phenyl]carbamate

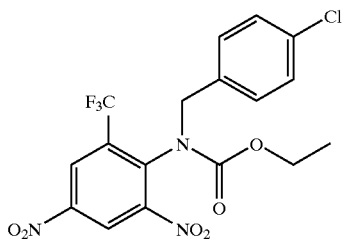

Ethyl 4-chlorobenzylcarbamate (865.9 mg) and 2-chloro-3,5-dinitrobenzotrifluoride (996.7 mg) were dissolved in tetrahydrofuran (15 ml), and to the solution was added sodium hydride (162.1 mg). The reaction mixture was heated at reflux for 3 hours. After allowing to cool, to the reaction mixture was added 1N hydrochloric acid, and the mixture was extracted with ethyl acetate. The organic layer was washed with saturated brine, dried over anhydrous magnesium sulfate, and concentrated in vacuo. The resultant residue was purified by silica gel column (75 g, hexane:ethyl acetate=10:1) to give the title compound (294.7 mg, 18%).

$^1$H-NMR (CDCl$_3$, 300 MHz) δ 1.15 (3H, t, J=7.1 Hz), 4.19 (2H, dq, J=7.0, 1.5 Hz), 4.30 (1H, d, J=14.6 Hz), 5.19 (1H, d, J=14.6 Hz), 7.07 (2H, d, J=8.4 Hz), 7.19 (2H, d, J=8.4 Hz), 8.82 (2H, s).

Example 4-3

Synthesis of ethyl 4-chlorobenzyl[2,4-diamino-6-(trifluoromethyl)phenyl]carbamate

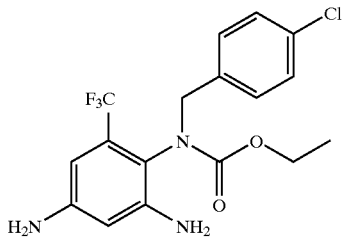

Ethyl 4-chlorobenzyl[2,4-dinitro-6-(trifluoromethyl)phenyl]carbamate (294.7 mg) was dissolved in ethyl acetate (20 ml), and to the solution was added 10% Pd—C (267.7 mg). The reaction mixture was stirred under hydrogen atmosphere for 7 hours. The catalyst was filtered, and washed with ethyl acetate. The filtrate was concentrated in vacuo to give the title compound (248.7 mg).

Example 4-4

Synthesis of 5-amino-1-(4-chlorobenzyl)-7-(trifluoromethyl)-1,3-dihydro-2H-benzimidazol-2-one

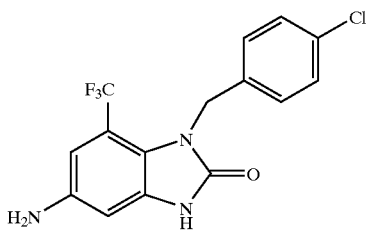

Ethyl 4-chlorobenzyl[2,4-diamino-6-(trifluoromethyl)phenyl]carbamate (248.7 mg) was dissolved in ethanol (15 ml), and to the solution was added sodium hydride (51.3 mg). The reaction mixture was heated at reflux for 15 hours. After allowing to cool, to the reaction mixture was added saturated aqueous sodium bicarbonate solution, and the mixture was extracted 3 times with chloroform. The organic layer was washed with saturated brine, dried over anhydrous sodium sulfate, and concentrated in vacuo. The resultant residue was purified by preparative TLC (2 mm, 20×20 cm, CHCl$_3$-methanol=10:1) to give the title compound (78.4 mg).

Example 4-5

Synthesis of 1-(4-chlorobenzyl)-3-[2-(diethylamino)ethyl]-2-oxo-7-(trifluoromethyl)-2,3-dihydro-1H-benzimidazole-5-carboxamide trifluoroacetate

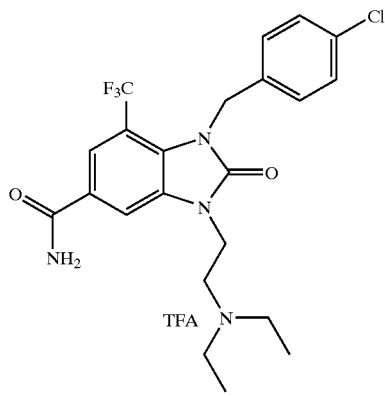

5-Amino-1-(4-chlorobenzyl)-7-(trifluoromethyl)-1,3-dihydro-2H-benzimidazol-2-one (78.4 mg) was dissolved in dimethyl sulfoxide (2 ml), and to the solution was added CuCN (26.7 mg). The mixture was heated at 55+ C. At the same temperature, a solution of t-butyl nitrite (71.0 mg) in dimethyl sulfoxide (1 ml) was added dropwise during 2 hours. After the addition was completed, the mixture was stirred at 60° C. for 2 hours. After allowing to cool, to the reaction mixture was added saturated brine, and the mixture was extracted with ethyl acetate. The organic layer was washed with saturated brine, dried over anhydrous magnesium sulfate, and concentrated in vacuo. The resultant residue was dissolved in N,N-dimethylformamide (2 ml), and to the solution was added sodium hydride (11.9 mg). The mixture was stirred at room temperature for 5 minutes. A solution of 2-chlorotriethylamine hydrochloride (51.3 mg) in N,N-dimethylformamide (2 ml) and triethylamine (0.048 ml) were added, and the mixture was stirred at 70–80° C. for 3.5 hours. After allowing to cool, to the reaction mixture was added saturated aqueous sodium bicarbonate solution, and the mixture was extracted with ethyl acetate. The organic layer was washed with saturated brine, dried over anhydrous sodium sulfate, and concentrated in vacuo. The resultant residue was dissolved in 2-methyl-2-propanol (4 ml) and heated at 50° C. To the solution was added powdered potassium hydroxide (322 mg), and the mixture was stirred for 1 hour. After allowing to cool, to the reaction mixture was added saturated aqueous sodium bicarbonate solution, and the mixture was extracted with ethyl acetate. The organic layer was washed with saturated brine, dried over anhydrous sodium sulfate, and concentrated in vacuo. The resultant residue was purified by HPLC using condition 1 to give the title compound (2.6 mg, 2%).

$^1$H-NMR (DMSO-$d_6$, 300 MHz) δ 1.18 (6H, m), 3.60–3.40 (6H, m), 4.36 (2H, brs), 5.21 (2H, s), 7.15–7.09 (2H, m), 7.37–7.33 (2H, m), 7.59 (1H, brs), 7.99 (1H, s), 8.16 (2H, s), 9.28 (1H, brs). HPLC retention time: 17.9 min. (condition 1).

Example 5

Synthesis of 1-(2-chlorobenzyl)-3-[2-(diethylamino)ethyl]-2-oxo-7-(trifluoromethyl)-2,3-dihydro-1H-benzimidazole-5-carboxamide trifluoroacetate Example 5-1

Synthesis of ethyl 4-bromo-2-(trifluoromethyl)phenylcarbamate

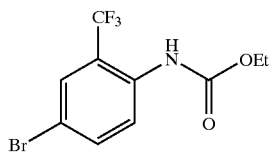

After to a solution of 4-bromo-2-trifluoromethylaniline (2.805 ml) in pyridine (15 ml) was added dropwise ethyl chloroformate (2.130 ml) during 15 minutes in an ice bath, the reaction mixture was stirred for 40 minutes. Then, to the solution was added dropwise ethyl chloroformate (1.000 ml) during 5 minutes in an ice bath again. The reaction mixture was stirred for 1 hour. After to the reaction solution was added water, 1N hydrochloric acid was added and the mixture was extracted with ethyl acetate. The organic layer was washed with 1N hydrochloric acid, saturated brine, saturated aqueous sodium bicarbonate solution, and then saturated brine, dried over anhydrous magnesium sulfate, and concentrated in vacuo to give the title compound (6.4509 g, quantitative yield).

$^1$H-NMR (CDCl$_3$, 300 MHz) δ 1.33 (3H, t, J=7.2 Hz), 4.25 (2H, q, J=7.2 Hz), 6.88 (1H, brs), 7.64 (1H, dd, J=9.0, 2.4 Hz), 7.70 (1H, d, J=2.4 Hz), 8.09 (1H, d, J=8.8 Hz). HPLC retention time: 32.96 min. (condition 2).

Example 5-2

Synthesis of ethyl 4-bromo-2-nitro-6-(trifluoromethyl)phenylcarbamate

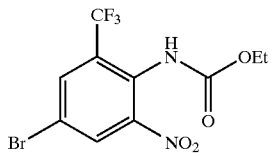

To acetic anhydride (10 ml) was added dropwise conc. nitric acid (d=1.42, 1.300 ml) during 10 minutes in an ice bath and added one drop of conc. sulfuric acid (96%). To this solution was added a solution of ethyl 4-bromo-2-(trifluoromethyl)phenylcarbamate in acetic anhydride (7 ml)/acetic acid (1 ml) during 30 minutes in an ice bath. After stirring for 2.5 hours, the reaction mixture was poured into ice-water, and the precipitated solid product was filtered. The resultant solid product was purified by silica gel column (120 g, hexane:ethyl acetate=15:1) to give the title compound (2.3265 g, 61%).

$^1$H-NMR (CDCl$_3$, 300 MHz) δ 1.29 (3H, t, J=6.6 Hz), 4.22 (2H, q, J=7.0 Hz), 6.81 (1H, br), 8.0–1 (1H, d, J=2.4 Hz), 8.24 (1H, d, J=2.2 Hz). HPLC retention time: 30.12 min. (condition 2).

0132

Example 5-3

Synthesis of ethyl 4-bromo-2-nitro-6-(trifluoromethyl)phenyl(2-chlorobenzyl)carbamate

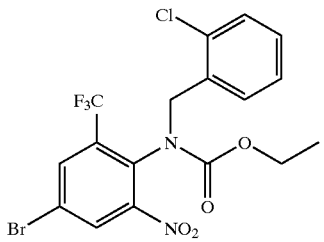

Ethyl 4-bromo-2-nitro-6-(trifluoromethyl)phenylcarbamate (475.5 mg) was dissolved in N,N-dimethylformamide (10 ml), and to the solution were added potassium carbonate (220.9 mg) and 2-chlorobenzyl bromide (0.207 ml). Then the mixture was heated at 50° C. and stirred for 1 hour. After allowing to cool, to the reaction mixture was added saturated brine, and the mixture was extracted with ethyl acetate. The organic layer was washed with saturated brine, dried over anhydrous magnesium sulfate, and concentrated in vacuo to give the title compound (757.2 mg, quantitative yield).

$^1$H-NMR (CDCl$_3$, 300 MHz) δ 1.13 (3H, t, J=7.1 Hz), 4.18 (2H, dq, J=7.1, 2.4 Hz), 4.62 (1H, d, J=14.7 Hz), 5.26 (1H, d, J=14.7 Hz), 7.28–7.18 (3H, m), 7.56–7.52 (1H, m), 8.09 (1H, d, J=2.3 Hz), 8.11 (1H, d, J=2.3 Hz).

Example 5-4

Synthesis of ethyl 2-chlorobenzyl[4-cyano-2-nitro-6-(trifluoromethyl)phenyl]carbamate

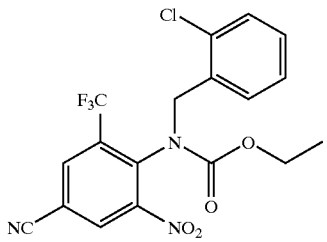

Ethyl 4-bromo-2-nitro-6-(trifluoromethyl)phenyl(2-chlorobenzyl)carbamate (620.3 mg) was dissolved in N,N-dimethylformamide (30 ml), and to the solution were added zinc cyanide (302.4 mg) and tetrakis(triphenylphosphine)palladium(0) (1.116 g). The mixture was heated at 60° C. and stirred for 7 hours. After allowing to cool, to the reaction mixture was added 1N hydrochloric acid, and the mixture was extracted with ethyl acetate. The organic layer was washed with saturated brine, dried over anhydrous magnesium sulfate, and concentrated in vacuo. The resultant residue was purified by silica gel column (100 g, hexane:ethyl acetate=3:1) to give the title compound (322.6 mg, 59%).

$^1$H-NMR (CDCl$_3$, 300 MHz) δ 1.13 (3H, t, J=7.0 Hz), 4.19 (2H, dq, J=7.1, 2.4 Hz), 4.66 (1H, d, J=14.9 Hz), 5.29 (1H, d, J=14.8 Hz), 7.28–7.18 (3H, m), 7.58–7.55 (1H, m), 8.24 (1H, d, J=2.0 Hz), 8.27 (1H, d, J=2.0 Hz).

Example 5-5

Synthesis of ethyl 2-amino-4-cyano-6-(trifluoromethyl)phenyl(2-chlorobenzyl)carbamate

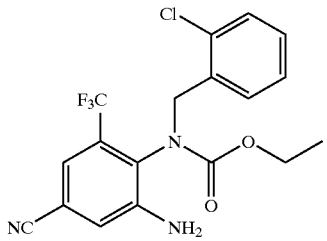

Ethyl 2-chlorobenzyl[4-cyano-2-nitro-6-(trifluoromethyl)phenyl]carbamate (298.4 mg) was dissolved in methanol (30 ml), and to the solution were added titanium(III) chloride solution (6.672 g) under ice-cooling. After stirring for 20 minutes, to the reaction mixture was added saturated aqueous sodium bicarbonate solution, and the mixture was extracted with ethyl acetate. The organic layer was washed with saturated brine, dried over anhydrous magnesium sulfate, and concentrated in vacuo to give the title compound (315.4 mg, quantitative yield).

$^1$H-NMR (CDCl$_3$, 300 MHz) δ 1.15–1.08 (3H, m), 3.06 (1H, s), 3.81 (1H, brs), 4.21–4.02 (2H, m), 4.51–4.39 (1H, m), 5.53–5.41 (1H, m), 7.69–7.00 (6H, m).

Example 5-6

Synthesis of 1-(2-chlorobenzyl)-2-oxo-7-(trifluoromethyl)-2,3-dihydro-1H-benzimidazole-5-carbonitrile

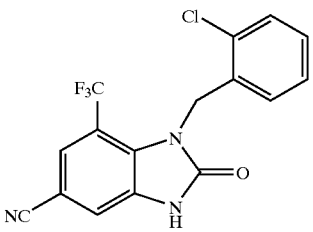

Ethyl 2-amino-4-cyano-6-(trifluoromethyl)phenyl(2-chlorobenzyl)carbamate (338.7 mg) was dissolved in ethanol (20 ml), and to the solution was added sodium hydride (37.5 mg). The reaction mixture was heated at reflux for 1 hour. After allowing to cool, to the reaction mixture was added 1N hydrochloric acid, and the mixture was extracted 4 times with chloroform. The organic layer was washed with saturated brine, dried over anhydrous magnesium sulfate, and concentrated in vacuo to give the title compound (287.0 mg, 96%).

$^1$H-NMR (CDCl$_3$, 300 MHz) δ 5.16 (2H, s), 6.70 (1H, dd, J=7.68, 1.29 Hz), 7.21 (1H, dt, J=7.68, 1.29 Hz), 7.29 (1H, dt, J=7.68, 1.47 Hz), 7.50 (1H, dd, J=7.68, 1.47 Hz), 7.82 (1H, d, J=1.47 Hz), 7.88 (1H, d, J=1.29 Hz), 12.23 (1H, s).

Example 5-7

Synthesis of 1-(2-chlorobenzyl)-3-[2-(diethylamino)ethyl]-2-oxo-7-(trifluoromethyl)-2,3-dihydro-1H-benzimidazole-5-carboxamide trifluoroacetate

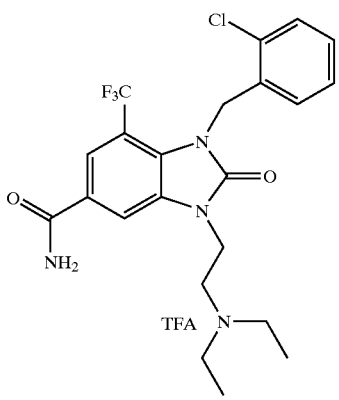

1-(2-Chlorobenzyl)-2-oxo-7-(trifluoromethyl)-2,3-dihydro-1H-benzimidazole-5-carbonitrile (280.6 mg) was dissolved in N,N-dimethylformamide (50 ml), and to the solution was added sodium hydride (41.5 mg). The reaction mixture was stirred under ice-cooling for 10 minutes. 2-Chlorotriethylamine hydrochloride (178.5 mg) and triethylamine (0.167 ml) were added, and the mixture was stirred at 70° C. for 18 hours. After allowing to cool, to the reaction mixture was added saturated aqueous sodium bicarbonate solution, and the mixture was extracted with ethyl acetate. The organic layer was washed with saturated brine, dried over anhydrous sodium sulfate, and concentrated in vacuo. The resultant residue was dissolved in 2-methyl-2- propanol (30 ml) and heated at 50° C. To the solution was added powdered potassium hydroxide (1.119 g), and the mixture was stirred for 1 hour. After allowing to cool, to the reaction mixture was added saturated aqueous sodium bicarbonate solution, and the mixture was extracted with ethyl acetate. The organic layer was washed with saturated brine, dried over anhydrous sodium sulfate, and concentrated in vacuo. The resultant residue was purified by HPLC using condition 1 to give the title compound (280.9 mg, 60%).

$^1$H-NMR (DMSO-$d_6$, 300 MHz) δ 1.10 (6H, brs), 3.80–2.90 (6H, m), 4.40–4.10 (2H, m), 5.22 (2H, s), 6.78 (1H, d, J=7.3 Hz), 7.19 (1H, t, J=7.3 Hz), 7.30 (1H, t, J=7.3 Hz), 7.64–7.50 (3H, m), 7.98 (1H, s), 8.19 (1H, brs), 8.23 (1H, s). HPLC retention time: 17.6 min. (condition 1).

Example 6

Synthesis of 1-(3-chlorophenyl)-3-[2-(diethylamino)ethyl]-2-oxo-7-(trifluoromethyl)-2,3-dihydro-1H-benzimidazole-5-carboxamide trifluoroacetate

Example 6-1

Synthesis of ethyl 3-chlorophenylcarbamate

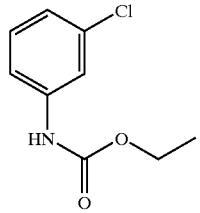

3-Chloroaniline (2.510 g) was dissolved in pyridine (20 ml), and to the solution was added dropwise ethyl chloroformate (2.257 ml) under ice-cooling. After the mixture was stirred for 1 hour, 1N hydrochloric acid was added and the mixture was extracted with ethyl acetate. The organic layer was washed with 1N hydrochloric acid, and then saturated brine, dried over anhydrous magnesium sulfate, and concentrated in vacuo to give the title compound (3.9287 g, quantitative yield).

$^1$H-NMR (CDCl$_3$, 300 MHz) δ 1.29 (3H, t, J=7.1 Hz), 4.22 (2H, q, J=7.1 Hz), 7.01 (2H, dt, J=7.3, 2.0 Hz), 7.25–7.16 (2H, m), 7.51 (1H, s).

Example 6-2

Synthesis of ethyl 3-chlorophenyl[2,4-dinitro-6-(trifluoromethyl)phenyl]carbamate

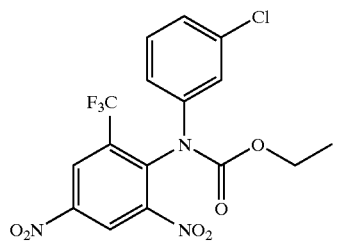

Ethyl 3-chlorophenylcarbamate (1.0256 g) was dissolved in diglyme (3 ml), and to the solution were added sodium hydride (205.5 mg) and 2-chloro-3,5-dinitrobenzotrifluoride (1.1583 g). The reaction mixture was stirred at room temperature for 4 hours. To the reaction mixture was added 1N hydrochloric acid, and the mixture was extracted with ethyl acetate. The organic layer was washed with 1N hydrochloric acid, saturated aqueous sodium bicarbonate solution, and then saturated brine, dried over anhydrous magnesium sulfate, and concentrated in vacuo. The resultant residue was purified by silica gel column (75 g, hexane:ethyl acetate= 5:1) and recrystallized from hexane-ethyl acetate to give the title compound (0.7854 g, 42%).

$^1$H-NMR (CDCl$_3$, 300 MHz) δ 1.21 (3H, brs), 4.24 (2H, brs), 7.03 (1H, dt, J=7.7, 1.8 Hz), 7.27–7.18 (3H, m), 8.86 (1H, d, J=2.7 Hz), 9.05 (1H, d, J=2.7 Hz).

Example 6-3

Synthesis of ethyl 3-chlorophenyl[2,4-diamino-6-(trifluoromethyl)phenyl]carbamate

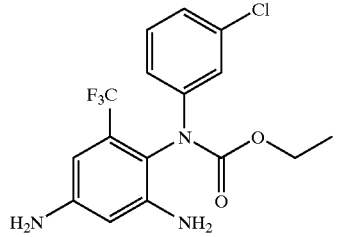

Ethyl 3-chlorophenyl[2,4-dinitro-6-(trifluoromethyl)phenyl]carbamate. (0.7111 g) was dissolved in methanol (40 ml), and to the solution was added titanium(III) chloride solution (15.175 g) under ice-cooling. After stirring for 2 hours, to the reaction mixture was added saturated aqueous sodium bicarbonate solution (350 ml), and the mixture was extracted 2 times with ethyl acetate. The organic layer was washed with saturated brine, dried over anhydrous magnesium sulfate, and concentrated in vacuo. The resultant residue was purified by silica gel column (70 g, CHCl$_3$:methanol=10:1) to give the title compound (0.6589 g, quantitative yield).

$^1$H-NMR (CDCl$_3$, 300 MHz) δ 1.19 (3H, t, J=7.1 Hz), 3.79 (4H, brs), 4.21 (2H, q, J=7.1 Hz), 6.23 (1H, d, J=2.6 Hz), 6.41 (1H, d, J=2.6 Hz), 7.05 (1H, ddd, J=7.7, 2.0, 1.3 Hz), 7.17 (1H, t, J=8.2 Hz), 7.23 (1H, dd, J=2.0, 1.3 Hz), 7.44 (1H, t, J=2.0 Hz).

Example 6-4

Synthesis of 5-amino-1-(3-chlorophenyl)-7-(trifluoromethyl)-1,3-dihydro-2H-benzimidazol-2-one

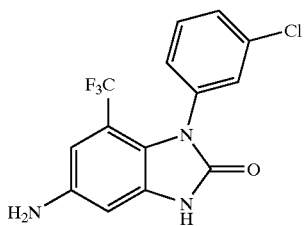

Ethyl 3-chlorophenyl[2,4-diamino-6-(trifluoromethyl)phenyl]carbamate (80.2 mg) was dissolved in ethanol (1 ml), and to the solution was added sodium hydride (8.6 mg). The reaction mixture was heated at reflux for 2.5 hours. After allowing to cool, to the reaction mixture was added saturated aqueous sodium bicarbonate solution, and the mixture was extracted with ethyl acetate. The organic layer was washed with saturated brine, dried over anhydrous magnesium sulfate, and concentrated in vacuo. The resultant residue was purified by preparative TLC (2 mm, 20×20 cm, CHCl$_3$-methanol=10:1) to give the title compound (20.6 mg, 29%).

$^1$H-NMR (DMSO-d$_6$, 300 MHz) δ 5.27 (2H, brs), 6.52 (1H, d, J=2.2 Hz), 6.59 (1H, d, J=1.8 Hz), 7.30–7.26 (1H, m), 7.42 (1H, s), 7.52–7.47 (2H, m).

Example 6-5

Synthesis of 1-(3-chlorophenyl)-2-oxo-7-(trifluoromethyl)-2,3-dihydro-1H-benzimidazole-5-carbonitrile

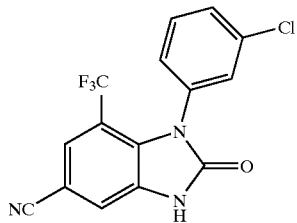

5-Amino-1-(3-chlorophenyl)-7-(trifluoromethyl)-1,3-dihydro-2H-benzimidazol-2-one (125.1 mg) was dissolved in dimethyl sulfoxide (5 ml), and to the solution was added CuCN (102.6 mg). The mixture was heated at 55° C. At the same temperature, t-butyl nitrite (0.134 ml) was added dropwise during 30 minutes. After the addition was completed, the mixture was stirred at 60° C. for 1 hour. After allowing to cool, to the reaction mixture was added water, and the mixture was extracted with ethyl acetate. The organic layer was washed with saturated brine, dried over anhydrous magnesium sulfate, and concentrated in vacuo. The resultant residue was purified by preparative TLC (2 mm, 20×20 cm, CHCl$_3$:methanol=10:1) and then preparative TLC (2 mm, 20×20 cm, hexane:ethyl acetate=2:1) to give the title compound (31.4 mg, 24%).

$^1$H-NMR (CDCl$_3$, 300 MHz) δ 7.66–7.16 (6H, m), 11.31 (1H, s).

Example 6-6

Synthesis of 1-(3-chlorophenyl)-3-[2-(diethylamino)ethyl]-2-oxo-7-(trifluoromethyl)-2,3-dihydro-1H-benzimidazole-5-carboxamide trifluoroacetate

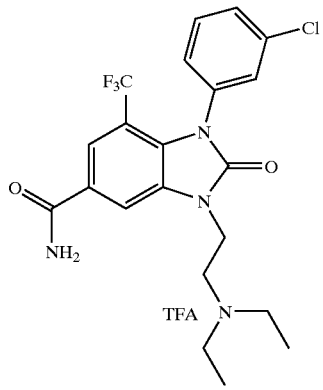

1-(3-Chlorophenyl)-2-oxo-7-(trifluoromethyl)-2,3-dihydro-1H-benzimidazole-5-carbonitrile (31.4 mg) was dissolved in N,N-dimethylformamide (3 ml), and to the solution was added sodium hydride (4.8 mg). The mixture was stirred at room temperature for 5 minutes. 2-Chlorotriethylamine hydrochloride (20.8 mg) and triethylamine (0.019 ml) were added, and the mixture was stirred at 60–70° C. for 1 hour. After allowing to cool, to the reaction mixture was added saturated aqueous sodium bicarbonate solution, and the mixture was extracted with ethyl acetate. The organic layer was washed with saturated brine, dried over anhydrous sodium sulfate, and concentrated in vacuo. The resultant residue was dissolved in 2-methyl-2-propanol (4 ml) and heated at 50° C. To the solution was added powdered potassium hydroxide (130.4 mg), and the mixture was stirred for 1 hour. After allowing to cool, to the reaction mixture was added saturated aqueous sodium bicarbonate solution, and the mixture was extracted with ethyl acetate. The organic layer was washed with saturated brine, dried over anhydrous sodium sulfate, and concentrated in vacuo. The resultant residue was purified by HPLC using condition 1 to give the title compound (20.0 mg, 38%).

$^1$H-NMR (DMSO-d$_6$, 300 MHz) δ 1.20 (6H, brs), 3.40–3.20 (4H, m), 3.60–3.45 (2H, m), 4.34 (2H, brs), 7.42 (1H, d, J=7.7 Hz), 7.65–7.55 (4H, m), 7.97 (1H, brs), 8.20–8.14 (2H, m), 9.37 (1H, brs). HPLC retention time: 15.6 min. (condition 1).

Example 7

Synthesis of 1-(4-chlorophenyl)-3-[2-(diethylamino) ethyl]-2-oxo-7-(trifluoromethyl)-2,3-dihydro-1H-benzimidazole-5-carboxamide trifluoroacetate

Example 7-1

Synthesis of ethyl 4-chlorophenylcarbamate

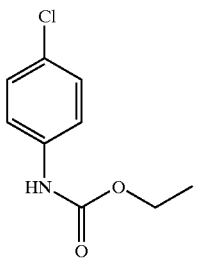

4-Chloroaniline (2.3531 g) was dissolved in pyridine (20 ml), and to the solution was added dropwise ethyl chloroformate (2.116 ml) under ice-cooling. After the mixture was stirred for 1.5 hours, 1N hydrochloric acid was added and the mixture was extracted with ethyl acetate. The organic layer was washed with 1N hydrochloric acid, and then saturated brine, dried over anhydrous magnesium sulfate, and concentrated in vacuo to give the title compound (3.6875 g, quantitative yield).

$^1$H-NMR (CDCl$_3$, 300 MHz) δ 1.30 (3H, t, J=7.1 Hz), 4.22 (2H, q, J=7.1 Hz), 6.79 (1H, brs), 7.34–7.22 (4H, m).

Example 7-2

Synthesis of ethyl 4-chlorophenyl[2,4-dinitro-6-(trifluoromethyl)phenyl]carbamate

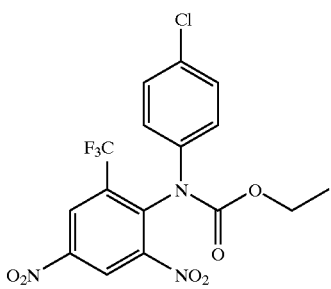

Ethyl 4-chlorophenylcarbamate (1.2281 g) was dissolved in tetrahydrofuran (30 ml), and to the solution were added sodium hydride (246.1 mg) and 2-chloro-3,5-dinitrobenzotrifluoride (1.3870 g). The reaction mixture was stirred at room temperature for 2 hours. To the reaction mixture was added 1N hydrochloric acid, and the mixture was extracted with ethyl acetate. The organic layer was washed with saturated brine, dried over anhydrous magnesium sulfate, and concentrated in vacuo. The resultant residue was purified by silica gel column (75 g, hexane:ethyl acetate=5:1) to give the title compound (1.7323 g, 78%).

$^1$H-NMR (CDCl$_3$, 300 MHz) δ 1.20 (3H, brs), 4.23 (2H, brs), 7.12 (2H, d, J=8.8 Hz), 7.27 (2H, d, J=8.6 Hz), 8.84 (1H, d, J=2.4 Hz), 9.02 (1H, d, J=2.5 Hz).

Example 7-3

Synthesis of ethyl 4-chlorophenyl[2,4-diamino-6-(trifluoromethyl)phenyl]carbamate

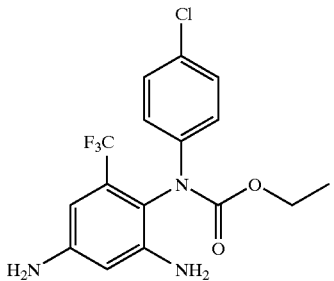

Ethyl 4-chlorophenyl[2,4-dinitro-6-(trifluoromethyl) phenyl]carbamate (1.7323 g) was dissolved in methanol (100 ml), and to the solution was added titanium(III) chloride solution (36.967 g) under ice-cooling. The reaction mixture was stirred for 2 hours. To the reaction mixture was added saturated aqueous sodium bicarbonate solution (800 ml), and the mixture was extracted 2 times with ethyl acetate. The organic layer was washed with saturated brine, dried over anhydrous magnesium sulfate, and concentrated in vacuo. The resultant residue was purified by silica gel column (70 g, CHCl$_3$:methanol=10:1) to give the title compound (1.2292 g, 82%).

$^1$H-NMR (CDCl$_3$, 300 MHz) δ 1.19 (3H, t, J=7.1 Hz), 3.83 (4H, brs), 4.12 (2H, q, J=7.1 Hz), 6.22 (1H, d, J=2.4 Hz), 6.39 (1H, d, J=2.4 Hz), 7.21 (2H, d, J=9.1 Hz), 7.33 (2H, d, J=9.0 Hz).

Example 7-4

Synthesis of 5-amino-1-(4-chlorophenyl)-7-(trifluoromethyl)-1,3-dihydro-2H-benzimidazol-2-one

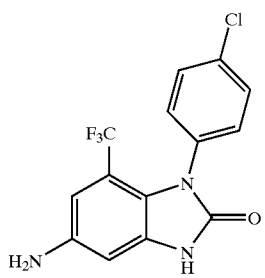

Ethyl 4-chlorophenyl[2,4-diamino-6-(trifluoromethyl) phenyl]carbamate (1.2053 g) was dissolved in ethanol (20 ml), and to the solution was added sodium hydride (129.0 mg). The reaction mixture was heated at reflux for 9 hours. After allowing to cool, to the reaction mixture was added saturated aqueous sodium bicarbonate solution, and the mixture was extracted with ethyl acetate. The organic layer was washed with saturated brine, dried over anhydrous magnesium sulfate, and concentrated in vacuo. The resultant residue was purified by silica gel column (60 g, CHCl$_3$:methanol=10:1→5:1) to give the title compound (0.7431 g, 70%).

$^1$H-NMR (DMSO-d$_6$, 300 MHz) δ 5.26 (2H, s), 6.51 (1H, d, J=2.2 Hz), 6.57 (1H, d, J=1.7 Hz), 7.33 (2H, d, J=8.6 Hz), 7.52 (2H, d, J=8.7 Hz), 11.17 (1H, s).

Example 7-5

Synthesis of 1-(4-chlorophenyl)-2-oxo-7-(trifluoromethyl)-2,3-dihydro-1H-benzimidazole-5-carbonitrile

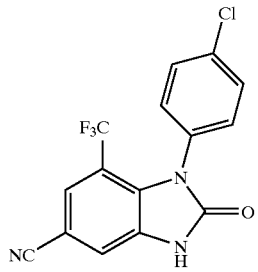

5-Amino-1-(4-chlorophenyl)-7-(trifluoromethyl)-1,3-dihydro-2H-benzimidazol-2-one (0.7398 g) was dissolved in dimethyl sulfoxide (35 ml), and to the solution was added CuCN (0.6065 g). The mixture was heated at 55° C. At the same temperature, t-butyl nitrite (0.792 ml) was added dropwise during 1.5 hours. After the addition was completed, the mixture was stirred at 60° C. for 4 hours. After allowing to cool, to the reaction mixture was added saturated brine, and the mixture was extracted with ethyl acetate. The organic layer was washed with saturated brine, dried over anhydrous magnesium sulfate, and concentrated in vacuo. The resultant residue was purified by silica gel column (100 g, CHCl$_3$:methanol=25:1) and then by silica gel column (70 g, hexane:ethyl acetate=1:1) to give the title compound (0.1767 g, 23%).

$^1$H-NMR (CDCl$_3$, 300 MHz) δ 7.67–7.14 (6H, m), 10.20 (1H, s).

Example 7-6

Synthesis of 1-(4-chlorophenyl)-3-[2-(diethylamino)ethyl]-2-oxo-7-(trifluoromethyl)-2,3-dihydro-1H-benzimidazole-5-carboxamide trifluoroacetate

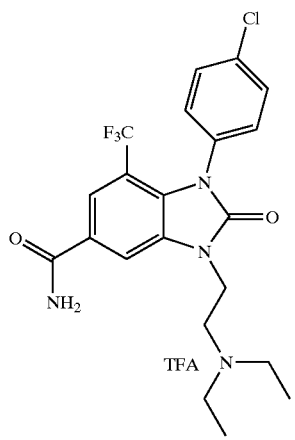

1-(4-Chlorophenyl)-2-oxo-7-(trifluoromethyl)-2,3-dihydro-1H-benzimidazole-5-carbonitrile (0.1767 g) was dissolved in N,N-dimethylformamide (5 ml), and to the solution was added sodium hydride (27.2 mg). The mixture was stirred at room temperature for 5 minutes. To the mixture were added 2-chlorotriethylamine hydrochloride (117.1 mg) and triethylamine (0.109 ml), and the mixture was stirred at 60–70° C. for 1 hour. After allowing to cool, to the reaction mixture was added saturated aqueous sodium bicarbonate solution, and the mixture was extracted with ethyl acetate. The organic layer was washed with saturated brine, dried over anhydrous sodium sulfate, and concentrated in vacuo. The resultant residue was dissolved in 2-methyl-2-propanol (15 ml) and heated at 50° C. To the solution was added powdered potassium hydroxide (0.7340 g), and the mixture was stirred for 1 hour. After allowing to cool, to the reaction mixture was added saturated aqueous sodium bicarbonate solution, and the mixture was extracted with ethyl acetate. The organic layer was washed with saturated brine, dried over anhydrous sodium sulfate, and concentrated in vacuo. The resultant residue was purified by HPLC using condition 1 to give the title compound (90.4 mg, 30%).

$^1$H-NMR (DMSO-d$_6$, 300 MHz) δ 1.20 (6H, t, J=7.0 Hz), 3.40–3.20 (4H, m), 3.60–3.45 (2H, m), 4.34 (2H, brs), 7.46 (2H, d, J=8.6 Hz), 7.66–7.60 (3H, m), 7.96 (1H, brs), 8.17 (2H, brs), 9.54 (1H, brs). HPLC retention time: 15.8 min (condition 1).

Example 8

Synthesis of 1-(2,4-dichlorophenyl)-3-[2-(diethylamino)ethyl]-2-oxo-7-(trifluoromethyl)-2,3-dihydro-1H-benzimidazole-5-carboxamide trifluoroacetate

Example 8-1

Synthesis of ethyl 2,4-dichlorophenylcarbamate

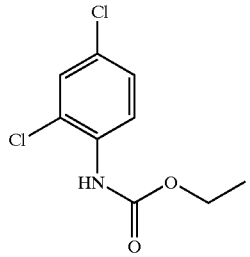

2,4-Dichloroaniline (2.380 g) was dissolved in pyridine (20 ml), and to the solution was added dropwise ethyl chloroformate (1.685 ml) under ice-cooling. After the mixture was stirred for 2 hours, 1N hydrochloric acid was added. The precipitated crystals were filtered, washed with water and then dried to give the title compound (3.4055 g, 99%).

$^1$H-NMR (CDCl$_3$, 300 MHz) δ 1.33 (3H, t, J=7.1 Hz), 4.25 (2H, q, J=7.1 Hz), 7.07 (1H, brs), 7.23 (1H, dd, J=9.0, 2.4 Hz), 7.35 (1H, d, J=2.4 Hz), 8.13 (1H, d, J=9.0 Hz).

Example 8-2

Synthesis of ethyl 2,4-dichlorophenyl[2,4-dinitro-6-(trifluoromethyl)phenyl]carbamate

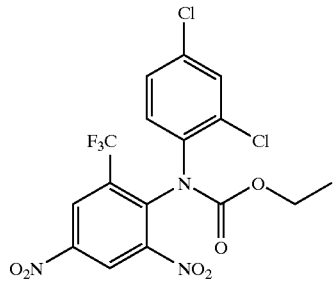

Ethyl 2,4-dichlorophenylcarbamate (1.206 g) was dissolved in tetrahydrofuran (15 ml), and to the solution were added sodium hydride (206.0 mg) and 2-chloro-3,5-dinitrobenzotrifluoride (1.161 g). The reaction mixture was stirred at room temperature for 4 hours. To the reaction mixture was added 1N hydrochloric acid, and the mixture was extracted with ethyl acetate. The organic layer was washed with saturated brine, dried over anhydrous magnesium sulfate, and concentrated in vacuo. The resultant residue was purified by silica gel column (75 g, hexane:ethyl acetate=5:1) to give the title compound (1.4490 g, 72%).

$^1$H-NMR (CDCl$_3$, 300 MHz) δ 1.38–1.15 (3H, m), 4.31–4.20 (2H, m), 7.26–6.97 (2H, m), 7.48–7.43 (1H, m), 8.80(1H, d, J=2.7 Hz), 9.00–8.97 (1H, m).

Example 8-3

Synthesis of ethyl 2,4-diamino-6-(trifluoromethyl)phenyl(2,4-dichlorophenyl)carbamate

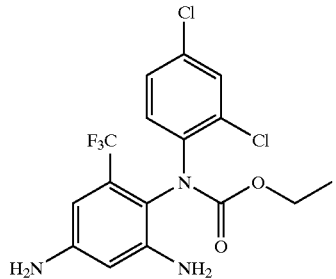

Ethyl 2,4-dichlorophenyl[2,4-dinitro-6-(trifluoromethyl)phenyl]carbamate (1.4027 g) was dissolved in methanol (80 ml), and to the solution was added titanium(III) chloride solution (27.731 g) under ice-cooling. The reaction mixture was stirred for 2 hours. To the reaction mixture was added saturated aqueous sodium bicarbonate solution (600 ml), and the mixture was extracted 2 times with ethyl acetate. The organic layer was washed with saturated brine, dried over anhydrous magnesium sulfate, and concentrated in vacuo to give the title compound (1.1863 g, 97%).

$^1$H-NMR (CDCl$_3$, 300 MHz) δ 1.25 (3H, t, J=7.1 Hz), 3.97 (4H, brs), 4.20 (2H, q, J=7.1 Hz), 6.12 (1H, d, J=2.4 Hz), 6.37 (1H, d, J=2.5 Hz), 7.08 (1H, s), 7.12 (1H, d, J=2.2 Hz), 7.42 (1H, d, J=2.4 Hz).

Example 8-4

Synthesis of 5-amino-1-(2,4-dichlorophenyl)-7-(trifluoromethyl)-1,3-dihydro-2H-benzimidazol-2-one

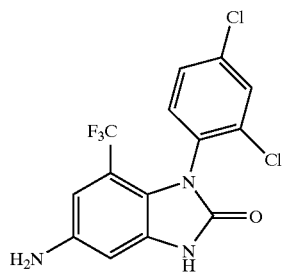

Ethyl 2,4-diamino-6-(trifluoromethyl)phenyl(2,4-dichlorophenyl)carbamate (1.1454 g) was dissolved in ethanol (20 ml), and to the solution was added sodium hydride (112.2 mg). The reaction mixture was heated at reflux for 6 hours. After allowing to cool, to the reaction mixture was added saturated aqueous sodium bicarbonate solution, and the mixture was extracted with ethyl acetate. The organic layer was washed with saturated brine, dried over anhydrous magnesium sulfate, and concentrated in vacuo. The resultant residue was purified by silica gel column (60 g, CHCl$_3$:methanol=10:1→5:1) to give the title compound (0.8058 g, 79%).

$^1$H-NMR (DMSO-d$_6$, 300 MHz) δ 5.28 (2H, s), 6.51 (1H, d, J=2.0 Hz), 6.59 (1H, d, J=1.7 Hz), 7.56–7.55 (2H, m), 7.83–7.82 (1H, m), 11.26 (1H, brs).

Example 8-5

Synthesis of 1-(2,4-dichlorophenyl)-2-oxo-7-(trifluoromethyl)-2,3-dihydro-1H-benzimidazole-5-carbonitrile

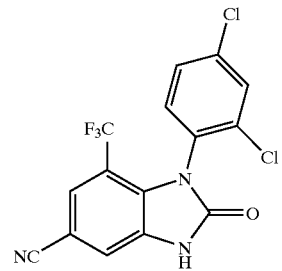

5-Amino-1-(2,4-dichlorophenyl)-7-(trifluoromethyl)-1,3-dihydro-2H-benzimidazol-2-one (0.7860 g) was dissolved in dimethyl sulfoxide (35 ml), and to the solution was added CuCN (0.5551 g). The mixture was heated at 55° C. At the same temperature, t-butyl nitrite (0.761 ml) was added dropwise during 1.5 hours. After the addition was completed, the mixture was stirred at 60° C. for 1.5 hours. After allowing to cool, to the reaction mixture was added saturated brine, and the mixture was extracted with ethyl acetate. The organic layer was washed with saturated brine, dried over anhydrous magnesium sulfate, and concentrated in vacuo. The resultant residue was purified by silica gel column (60 g, CHCl$_3$:methanol=10:1) and then by silica gel column (70 g, hexane:ethyl acetate=1:1) to give the title compound (0.1570 g, 19%).

$^1$H-NMR (CDCl$_3$, 300 MHz) δ 7.42 (1H, brs), 7.45 (1H, d, J=2.0 Hz), 7.51 (1H, d, J=1.5 Hz), 7.62 (1H, d, J=2.0 Hz), 7.67 (1H, d, J=1.0 Hz), 11.16 (1H, s).

Example 8-6

Synthesis of 1-(2,4-dichlorophenyl)-3-[2-(diethylamino)ethyl]-2-oxo-7-(trifluoromethyl)-2,3-dihydro-1H-benzimidazole-5-carboxamide trifluoroacetate

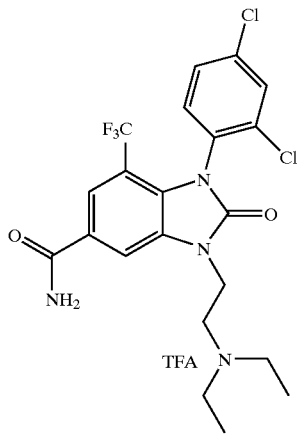

1-(2,4-Dichlorophenyl)-2-oxo-7-(trifluoromethyl)-2,3-dihydro-1H-benzimidazole-5-carbonitrile (0.1541 g) was dissolved in N,N-dimethylformamide (5 ml), and to the solution was added sodium hydride (21.5 mg). The mixture was stirred at room temperature for 5 minutes. To the mixture were added 2-chlorotriethylamine hydrochloride (92.6 mg) and triethylamine (0.087 ml), and the mixture was stirred at 60–70° C. for 15 hours. After allowing to cool, to the reaction mixture was added saturated aqueous sodium bicarbonate solution, and the mixture was extracted with ethyl acetate. The organic layer was washed with saturated brine, dried over anhydrous sodium sulfate, and concentrated in vacuo. The resultant residue was dissolved in 2-methyl-2-propanol (10 ml) and heated at 50° C. To the solution was added powdered potassium hydroxide (0.5810 g), and the mixture was stirred for 1 hour. After allowing to cool, to the reaction mixture was added saturated aqueous sodium bicarbonate solution, and the mixture was extracted with ethyl acetate. The organic layer was washed with saturated brine, dried over anhydrous sodium sulfate, and concentrated in vacuo. The resultant residue was purified by HPLC using condition 1 to give the title compound (88.3 mg, 35%).

$^1$H-NMR (DMSO-d$_6$, 300 MHz) δ 1.19 (6H, brs), 3.40–3.20 (4H, m), 3.60–3.45 (2H, m), 4.39 (2H, brs), 7.66–7.63 (3H, m), 7.98–7.95 (2H, m), 8.20 (2H, brs), 9.44 (1H, brs). HPLC retention time: 17.6 min (condition 1).

Example 9

Synthesis of 3-[2-(diethylamino)ethyl]-2-oxo-7-(trifluoromethyl)-1-[3-(trifluoromethyl)benzyl]-2,3-dihydro-1H-benzimidazole-5-carboxamide trifluoroacetate Example 9-1

Synthesis of ethyl 4-bromo-2-nitro-6-(trifluoromethyl)phenyl[3-(trifluoromethyl)benzyl] carbamate

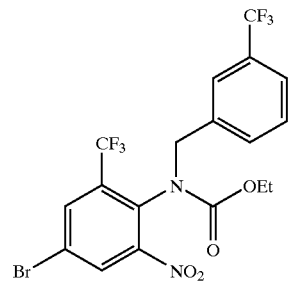

To a solution of ethyl 4-bromo-2-nitro-6-(trifluoromethyl)phenylcarbamate (275.3 mg) and potassium carbonate (108.3 mg) in N,N-dimethylformamide (5 ml) was added 3-trifluoromethylbenzyl bromide (0.180 ml). After the mixture was stirred at room temperature for 1 hour, 1N hydrochloric acid (ca. 30 ml) was added and the mixture was extracted with ethyl acetate. The organic layer was washed with 1N hydrochloric acid, saturated brine, saturated aqueous sodium bicarbonate solution, and then saturated brine, dried over anhydrous magnesium sulfate, and concentrated in vacuo. The resultant residue was purified by silica gel column (35 g, hexane:ethyl acetate=20:1) to give the title compound (345.3 mg, 82%).

$^1$H-NMR (CDCl$_3$, 300 MHz) δ 1.14 (3H, dt, J=7.2, 1.7 Hz), 4.19 (2H, dt, J=7.2, 1.5 Hz), 4.31 (1H, d, J=14.9 Hz), 5.20 (1H, d, J=14.9 Hz), 7.36–7.44 (3H, m), 7.54 (1H, d, J=7.2 Hz), 8.11 (2H, s). HPLC retention time: 39.45 min (condition 2).

Example 9-2

Synthesis of ethyl 2-amino-4-bromo-6-(trifluoromethyl)phenyl[3-(trifluoromethyl)benzyl] carbamate

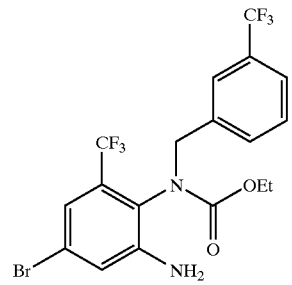

To a solution of ethyl 4-bromo-2-nitro-6-(trifluoromethyl) phenyl[3-(trifluoromethyl)benzyl]carbamate (225.7 mg) and nickel(II) chloride hexahydrate (211.9 mg) in methanol (5 ml) was added sodium borohydride (71.7 mg) in an ice bath.

After the mixture was stirred for 10 minutes, 1N hydrochloric acid was added. The mixture was basified with saturated aqueous sodium bicarbonate solution and the mixture was extracted with ethyl acetate. The organic layer was dried over anhydrous magnesium sulfate, and concentrated in vacuo to give the title compound (213.4 mg, quantitative yield).

$^1$H-NMR (CDCl$_3$, 300 MHz) δ 1.12 (3H, t, J=7.1 Hz), 3.54 (2H, brs), 4.00–4.28 (3H, m), 5.27 (1H, d, J=14.5 Hz), 6.98 (1H, brs), 7.16 (1H, brs), 7.40–7.45 (1H, m), 7.55–7.62 (3H, m). HPLC retention time: 39.59 min (condition 2).

Example 9-3

Synthesis of 5-bromo-7-(trifluoromethyl)-1-[3-(trifluoromethyl)benzyl]-1,3-dihydro-2H-benzimidazol-2-one

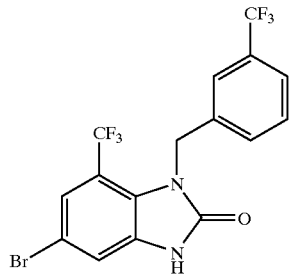

To a solution of ethyl 2-amino-4-bromo-6-(trifluoromethyl)phenyl[3-(trifluoromethyl)benzyl] carbamate (257.8 mg) in ethanol (10 ml) was added sodium hydride (60%) (48.7 mg). The reaction mixture was heated at reflux for 1.5 hours. To the reaction mixture was added 1N hydrochloric acid, and the mixture was extracted with chloroform. The organic layer was dried over anhydrous magnesium sulfate, and concentrated in vacuo to give the title compound (247.7 mg, quantitative yield).

$^1$H-NMR (CDCl$_3$, 300 MHz) δ 5.36 (2H, s), 7.26–7.28 (1H, m), 7.40–7.54 (5H, m), 10.57 (1H, s). HPLC retention time: 36.50 min (condition 2).

Example 9-4

Synthesis of 2-oxo-7-(trifluoromethyl)-1-[3-(trifluoromethyl)benzyl]-2,3-dihydro-1H-benzimidazole-5-carbonitrile

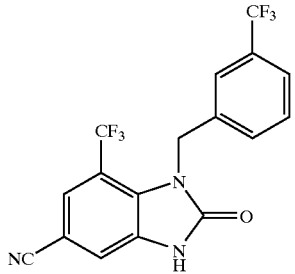

To a solution of 5-bromo-7-(trifluoromethyl)-1-[3-(trifluoromethyl)benzyl]-1,3-dihydro-2H-benzimidazol-2-one (171.9 mg) and copper(I) cyanide (76.3 mg) in N,N-dimethylformamide (10 ml) was heated at reflux for 11 hours. Copper(I) cyanide (51.0 mg) was further added, and the mixture was heated at reflux for 13 hours. To the reaction mixture was added saturated aqueous sodium bicarbonate solution, and the mixture was extracted 5 times with chloroform. The organic layer was dried over anhydrous magnesium sulfate, and concentrated in vacuo to give the title compound (139.5 mg, 93%).

$^1$H-NMR (CDCl$_3$, 300 MHz) δ 5.40 (2H, s), 7.26–7.30 (1H, m), 7.40–7.56 (3H, m), 7.58 (1H, d, J=1.3 Hz), 7.71 (1H, d, J=1.3 Hz), 10.72 (1H, s). HPLC retention time: 32.65 min (condition 2).

Example 9-5

Synthesis of 3-[2-(diethylamino)ethyl]-2-oxo-7-(trifluoromethyl)-1-[3-(trifluoromethyl)benzyl]-2,3-dihydro-1H-benzimidazole-5-carbonitrile

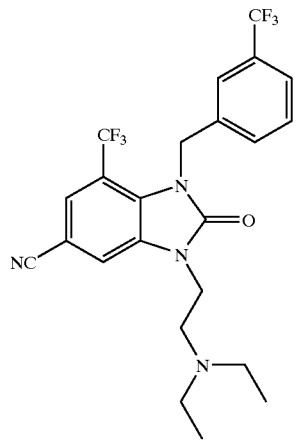

To a solution of 2-oxo-7-(trifluoromethyl)-1-[3-(trifluoromethyl)benzyl]-2,3-dihydro-1H-benzimidazole-5-carbonitrile (139.5 mg) in N,N-dimethylformamide (5 ml) was added sodium hydride (60%) (38.0 mg). After the mixture was stirred at room temperature for 10 minutes, 2-chlorotriethylamine hydrochloride (89.4 mg) and triethylamine (0.120 ml) were added, and the mixture was stirred with heating at 70° C. for 1.5 hours. To the reaction mixture was added 1N hydrochloric acid, and the mixture was basified with saturated aqueous sodium bicarbonate solution, and extracted with ethyl acetate. The organic layer was dried over anhydrous magnesium sulfate, and concentrated in vacuo to give the title compound (181 mg, quantitative yield).

1H-NMR (CDCl₃, 300 MHz) δ 0.92 (6H, t, J=7.1 Hz), 2.56 (4H, q, J=7.1 Hz), 2.79 (2H, t, J=6.1 Hz), 4.07 (2H, t, J=6.1 Hz), 5.39 (2H, s), 7.26–7.29 (1H, m), 7.38–7.43 (2H, m), 7.47–7.52 (1H, m), 7.62 (1H, d, J=1.3 Hz), 7.68 (1H, d, J=1.3 Hz). HPLC retention time: 29.83 min (condition 2).

Example 9-6

Synthesis of 3-[2-(diethylamino)ethyl]-2-oxo-7-(trifluoromethyl)-1-[3-(trifluoromethyl)benzyl]-2,3-dihydro-1H-benzimidazole-5-carboxamide trifluoroacetate

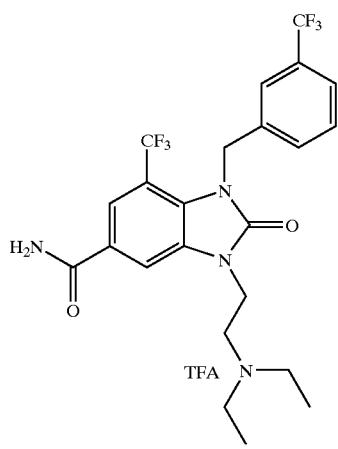

A solution of 3-[2-(diethylamino)ethyl]-2-oxo-7-(trifluoromethyl)-1-[3-(trifluoromethyl)benzyl]-2,3-dihydro-1H-benzimidazole-5-carbonitrile (226.3 mg) in t-butanol (10 ml) was stirred with heating at 60° C. To the solution was added powdered potassium hydroxide crashed in mortar (652.3 mg), and the mixture was stirred with heating at 60° C. for 2 hours. To the reaction mixture were added saturated aqueous sodium bicarbonate solution and water, and the mixture was extracted with ethyl acetate. The organic layer was dried over anhydrous magnesium sulfate, and concentrated in vacuo. The resultant residue was purified by HPLC using condition 2 to give the title compound (145.8 mg, 51%).

¹H-NMR (DMSO-d₆, 300 MHz) δ 1.20 (6H, t, J=7.2 Hz), 3.28 (4H, m), 3.55 (2H, m), 4.39 (2H, m), 5.29 (2H, s), 7.39 (1H, d, J=7.5 Hz), 7.53 (1H, t, J=7.5 Hz), 7.58–7.63 (3H, m), 8.00 (1H, d, J=1.1 Hz), 8.18 (1H, brs), 8.23 (1H, s), 9.50 (1H, brs). HPLC retention time: 26.17 min (condition 2). FAB-MS: 503 (M+H).

Example 10

Synthesis of 3-[2-(diethylamino)ethyl]-1-[2,4-(dimethoxy)benzyl]-2-oxo-7-(trifluoromethyl)-2,3-dihydro-1H-benzimidazole-5-carboxamide trifluoroacetate Example 10-1

Synthesis of ethyl 4-bromo-2-nitro-6-(trifluoromethyl)phenyl(2,4-dimethoxybenzyl)carbamate

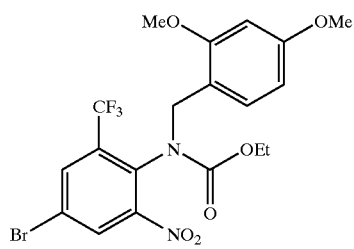

To a solution of ethyl 4-bromo-2-nitro-6-(trifluoromethyl)phenylcarbamate (1049.3 mg), 2,4-dimethoxybenzyl alcohol (1.7217 g) and triphenylphosphine (3.0183 g) in tetrahydrofuran (15 ml) was added diethyl azodicarboxylate (2.2505 g). The mixture was stirred at room temperature for 8 hours, and then concentrated in vacuo. The resultant residue was purified by silica gel column (110 g, hexane-:ethyl acetate=20:1→10:1) to give the title compound (796.8 mg, 53%) and recovered ethyl 4-bromo-2-nitro-6-(trifluoromethyl)phenylcarbamate (489.2 mg, 47%).

¹H-NMR (CDCl₃, 300 MHz) δ 1.11 (3H, t, J=7.2 Hz), 3.39 (3H, s), 3.78 (3H, s), 4.09–4.20 (2H, m), 4.40 (1H, d, J=14.1 Hz), 4.99 (1H, d, J=14.1 Hz), 6.22 (1H, d, J=2.4 Hz), 6.41 (1H, dd, J=8.3, 2.4 Hz), 7.23 (1H, d, J=8.3 Hz), 8.05 (1H, d, J=2.4 Hz), 8.15 (1H, d, J=2.2 Hz). HPLC retention time: 38.03 min (condition 2).

Example 10-2

Synthesis of ethyl 2-amino-4-bromo-6-(trifluoromethyl)phenyl(2,4-dimethoxybenzyl)carbamate

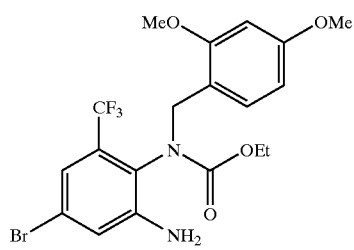

To a solution of ethyl 4-bromo-2-nitro-6-(trifluoromethyl)phenyl(2,4-dimethoxybenzyl)carbamate (1.204 g) in methanol (90 ml) was added titanium(III) chloride solution (20% wt) (31.5595 g) in an ice bath. The reaction mixture was stirred for 20 minutes at 0° C. To the reaction mixture were added saturated aqueous sodium bicarbonate solution and water, and the mixture was extracted 5 times with ethyl acetate. The organic layer was dried over anhydrous magnesium sulfate, and concentrated in vacuo to give the title compound (1.1345 g, quantitative yield).

$^1$H-NMR (CDCl$_3$, 300 MHz) δ 1.10 (3H, t, J=7.1 Hz), 3.60 (3H, s), 3.69 (2H, brs), 3.77 (3H, s), 3.99–4.21 (2H, m), 4.25 (1H, d, J=13.9 Hz), 5.23 (1H, d, J=14.1 Hz), 6.34–6.38 (2H, m), 6.86 (1H, d, J=1.8 Hz), 7.10 (1H, d, J=2.0 Hz), 7.23–7.27 (1H, m). HPLC retention time: 37.37 min (condition 2).

Example 10-3

Synthesis of 5-bromo-1-(2,4-dimethoxybenzyl)-7-(trifluoromethyl)-1,3-dihydro-2H-benzimidazol-2-one

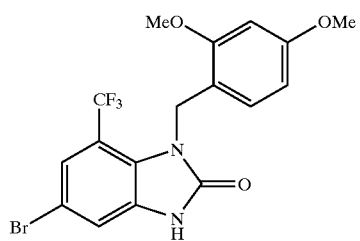

To a solution of ethyl 2-amino-4-bromo-6-(trifluoromethyl)phenyl(2,4-dimethoxybenzyl)carbamate (1.1345 g) in ethanol (75 ml) was added sodium hydride (60%) (225.5 mg). The reaction mixture was heated at reflux for 33 hours. The solvent was removed to about one third in vacuo. To the reaction mixture was added 1N hydrochloric acid, and the mixture was basified with saturated aqueous sodium bicarbonate solution, and extracted 5 times with ethyl acetate. The organic layer was dried over anhydrous magnesium sulfate, and concentrated in vacuo to give the title compound (1090.7 mg, quantitative yield). HPLC retention time: 34.49 min (condition 2).

Example 10-4

Synthesis of 1-(2,4-dimethoxybenzyl)-2-oxo-7-(trifluoromethyl)-2,3-dihydro-1H-benzimidazole-5-carbonitrile

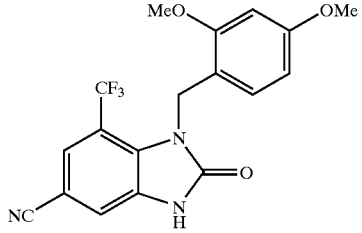

To a solution of 5-bromo-1-(2,4-dimethoxybenzyl)-7-(trifluoromethyl)-1,3-dihydro-2H-benzimidazol-2-one (1090.7 mg) and copper(I) cyanide (793.8 mg) in N,N-dimethylformamide (100 ml) was heated at reflux for 34 hours. The reaction mixture was concentrated in vacuo. To the resultant residue were added saturated aqueous sodium bicarbonate solution and water, and the mixture was extracted with ethyl acetate. The organic layer was dried over anhydrous magnesium sulfate, and concentrated in vacuo to give the title compound (1076.5 mg, quantitative yield). HPLC retention time: 30.54 min (condition 2).

Example 10-5

Synthesis of 3-[2-(diethylamino)ethyl]-1-[2,4-(dimethoxy)benzyl]-2-oxo-7-(trifluoromethyl)-2,3-dihydro-1H-benzimidazole-5-carbonitrile

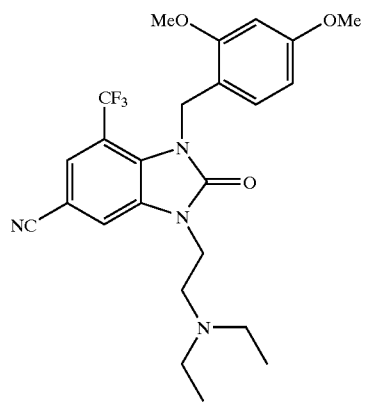

To a solution of 1-(2,4-dimethoxybenzyl)-2-oxo-7-(trifluoromethyl)-2,3-dihydro-1H-benzimidazole-5-carbonitrile (1076.5 mg) in N,N-dimethylformamide (60 ml) was added sodium hydride (60%) (461.7 mg). After the mixture was stirred at room temperature for 5 minutes, 2-chlorotriethylamine hydrochloride (996.1 mg) and triethylamine (1.770 ml) were added, and the mixture was stirred with heating at 70° C. for 2.5 hours. The reaction mixture was concentrated in vacuo. To the resultant residue were added ethyl acetate and 1N hydrochloric acid, and the mixture was basified with saturated aqueous sodium bicarbonate solution, and extracted with ethyl acetate. The organic layer was dried over anhydrous magnesium sulfate, and concentrated in vacuo. The resultant residue was purified by silica gel column (75 g, chloroform:methanol= 100:1→50:1) to give the title compound (615.0 mg).

¹H-NMR (CDCl₃, 300 MHz) δ 0.95 (6H, t, J=7.1 Hz), 2.57 (4H, q, J=7.1 Hz), 2.78 (2H, t, J=6.4 Hz), 3.75 (3H, s), 3.84 (3H, s), 4.04 (2H, t, J=6.4 Hz), 5.25 (2H, s), 6.27 (1H, dd, J=8.3, 2.3 Hz), 6.42–6.46 (2H, m), 7.55 (1H, brs), 7.66 (1H, d, J=1.3 Hz). HPLC retention time: 28.04 min (condition 2).

Example 10-6

Synthesis of 3-[2-(diethylamino)ethyl]-1-[2,3-(dimethoxy)benzyl]-2-oxo-7-(trifluoromethyl)-2,3-dihydro-1H-benzimidazole-5-carboxamide trifluoroacetate

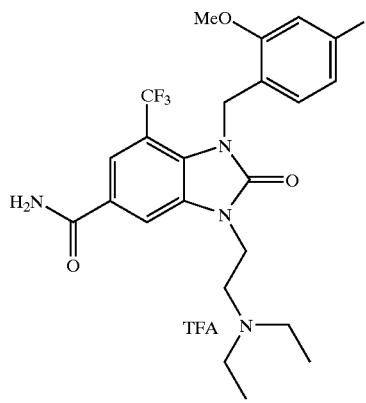

A solution of 3-[2-(diethylamino)ethyl]-1-[2,4-(dimethoxy)benzyl]-2-oxo-7-(trifluoromethyl)-2,3-dihydro-1H-benzimidazole-5-carbonitrile (13.5 mg) in t-butanol (3 ml) was stirred with heating at 60° C. To the solution was added powdered potassium hydroxide crashed in mortar (52.3 mg), and the mixture was stirred with heating at 60° C. for 1 hour. To the reaction mixture was added water, and the mixture was extracted with chloroform and then ethyl acetate. The organic layer was concentrated in vacuo. The resultant residue was purified by HPLC using condition 2 to give the title compound (6.1 mg, 35%).

¹H-NMR (DMSO-d₆, 300 MHz) δ 1.02–1.27 (6H, m), 3.69 (3H, s), 3.84 (3H, s), 4.17–4.40 (2H, m), 5.06 (2H, s), 6.31 (1H, dd, J=7.5, 2.9 Hz), 6.42 (1H, d, J=7.5 Hz), 6.59 (1H, d, J=2.9 Hz), 7.57 (1H, brs), 7.96 (1H, s), 8.17 (2H, brs). HPLC retention time: 23.91 min (condition 2). FAB-MS: 495 (M+H).

Example 11

Synthesis of 3-[2-(diethylamino)ethyl]-2-oxo-7-(trifluoromethyl)-1-[2-(trifluoromethyl)benzyl]-2,3-dihydro-1H-benzimidazole-5-carboxamide trifluoroacetate Example 11-1

Synthesis of 3-[2-(diethylamino)ethyl]-2-oxo-7-(trifluoromethyl)-2,3-dihydro-1H-benzimidazole-5-carbonitrile

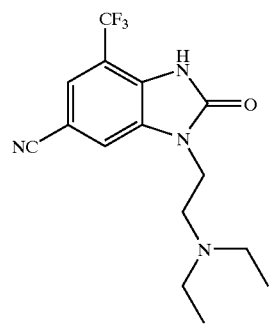

To a solution of 3-[2-(diethylamino)ethyl]-1-[2,4-(dimethoxy)benzyl]-2-oxo-7-(trifluoromethyl)-2,3-dihydro-1H-benzimidazole-5-carbonitrile (513.1 mg) in a mixed solvent of acetonitrile and water (3:1, 50 ml) was added ceric ammonium nitrate (IV) (1522.2 mg) in an ice bath. The mixture was stirred in an ice bath for 35 minutes and at room temperature for 100 minutes. Ceric ammonium nitrate (IV) (215.2 mg) was further added, and the mixture was stirred at room temperature for 45 minutes. To the reaction mixture were added saturated aqueous sodium bicarbonate solution and water, and the mixture as extracted 5 times with ethyl acetate. The organic layer as dried over anhydrous magnesium sulfate, and concentrated in vacuo. The resultant residue was purified by silica gel column (60 g, chloroform:methanol=50:1) to give the title compound (236.0 mg, 67%).

¹H-NMR (CDCl₃, 300 MHz) δ 0.98 (6H, t, J=7.1 Hz), 2.61 (4H, q, J=7.1 Hz), 2.80 (2H, t, J=6.5 Hz), 4.01 (2H, t, J=6.5 Hz), 7.51 (1H, s), 7.60 (1H, s). HPLC retention time: 17.40 min (condition 2).

Example 11-2

Synthesis of 3-[2-(diethylamino)ethyl]-2-oxo-7-(trifluoromethyl)-1-[2-(trifluoromethyl)benzyl]-2,3-dihydro-1H-benzimidazole-5-carbonitrile

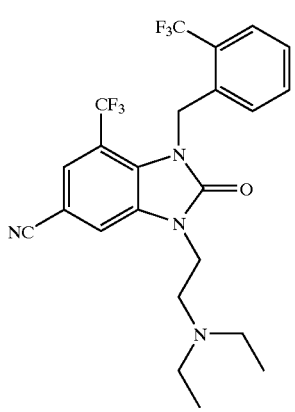

A mixture of 3-[2-(diethylamino)ethyl]-2-oxo-7-(trifluoromethyl)-2,3-dihydro-1H-benzimidazole-5-carbonitrile (19.1 mg), 2-trifluoromethylbenzyl bromide (30.4 mg) and potassium carbonate (16.5 mg) in N,N-dimethylformamide (3 ml) was stirred with heating at 80° C. for 1.5 hours. To the mixture was further added 2-trifluoromethylbenzyl bromide (46.8 mg), and the mixture was stirred with heating at 80° C. for 1 hour. 2-Trifluoromethylbenzyl bromide (160.3 mg) and potassium carbonate (43.2 mg) were further added, and the mixture was stirred with heating 80° C. for 1 hour. The reaction mixture was concentrated in vacuo. The resultant residue was purified by preparative TLC (1 mm, 20×20 cm, chloroform:methanol=25:1) to give the title compound (2.8 mg, 10%).

$^1$H-NMR (CDCl$_3$, 300 MHz) δ 0.97 (6H, t, J=7.2 Hz), 2.61 (4H, t, J=7.1 Hz), 2.83 (2H, t, J=6.2 Hz), 4.10 (2H, t, J=6.3 Hz), 5.57 (2H, s), 6.64–6.67 (1H, m), 7.32–7.38 (2H, m), 7.61 (1H, d, J=1.7 Hz), 7.68 (1H, d, J=1.7 Hz), 7.69–7.74 (1H, m). HPLC retention time: 30.06 min (condition 2).

Example 11-3

Synthesis of 3-[2-(diethylamino)ethyl]-2-oxo-7-(trifluoromethyl)-1-[2-(trifluoromethyl)benzyl]-2,3-dihydro-1H-benzimidazole-5-carboxamide trifluoroacetate

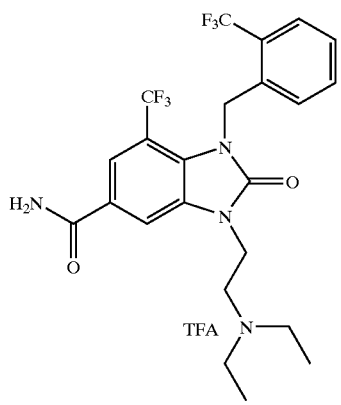

A solution of 3-[2-(diethylamino)ethyl]-2-oxo-7-(trifluoromethyl)-1-[2-(trifluoromethyl)benzyl]-2,3-dihydro-1H-benzimidazole-5-carbonitrile (2.8 mg) in t-butanol (2 ml) was stirred with heating at 60° C. To the solution was added powdered potassium hydroxide crashed in mortar (24.3 mg), and the mixture was stirred with heating at 60° C. for 30 minutes. To the reaction mixture was added 1N hydrochloric acid, and the mixture was concentrated in vacuo. The resultant residue was purified by HPLC using condition 2 to give the title compound (4.0 mg, quantitative yield).

$^1$H-NMR (DMSO-d$_6$, 300 MHz) δ 1.20 (6H, t, J=7.1 Hz), 3.52–3.59 (2H, m), 4.36–4.44 (2H, m), 5.37 (2H, s), 6.96–7.00 (1H, m), 7.46–7.56 (2H, m), 7.61 (1H, brs), 7.79–7.82 (1H, m), 8.00 (1H, s), 8.18 (1H, brs), 8.21 (1H, s), 9.17 (1H, brs). HPLC retention time: 26.34 min (condition 2). FAB-MS: 503 (M+H).

Example 12

Synthesis of 3-[2-(diethylamino)ethyl]-2-oxo-7-(trifluoromethyl)-1-[4-(trifluoromethyl)benzyl]-2,3-dihydro-1H-benzimidazole-5-carboxamide trifluoroacetate

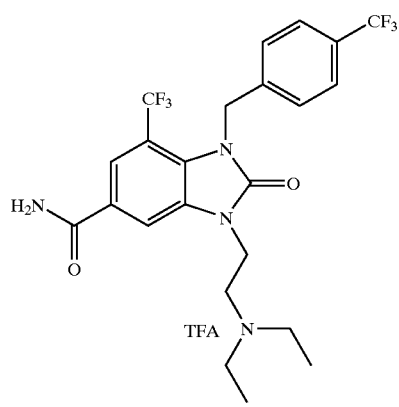

A solution of 3-[2-(diethylamino)ethyl]-2-oxo-7-(trifluoromethyl)-2,3-dihydro-1H-benzimidazole-5-carbonitrile (12.5 mg), 4-trifluoromethylbenzyl bromide (24.9 mg) and potassium carbonate (12.9 mg) in N,N-dimethylformamide (1.5 ml) was stirred with heating at 80° C. for 1.5 hours. The reaction mixture was concentrated in vacuo. To the resultant residue was added t-butanol (3 ml), and the mixture was stirred with heating at 60° C. To the solution was added powdered potassium hydroxide crashed in mortar (47.9 mg), and the mixture was stirred with heating at 60° C. for 45 minutes. To the reaction mixture was added 1N hydrochloric acid, and the mixture was concentrated in vacuo. The resultant residue was purified by HPLC using condition 2 to give the title compound (19.6 mg, 83%).

$^1$H-NMR (DMSO-$d_6$, 300 MHz) δ 1.20 (6H, t, J=7.2 Hz), 3.49–3.57 (2H, m), 4.34–4.41 (2H, m), 5.31 (2H, s), 7.35 (2H, d, J=8.4 Hz), 7.61 (1H, brs), 7.67 (2H, d, J=8.8 Hz), 8.01 (1H, s), 8.18 (2H, m). HPLC retention time: 26.49 min (condition 2). FAB-MS: 503 (M+H).

Example 13

Synthesis of 3-[2-(diethylamino)ethyl]-1-(2-fluorobenzyl)-2-oxo-7-(trifluoromethyl)-2,3-dihydro-1H-benzimidazole-5-carboxamide trifluoroacetate

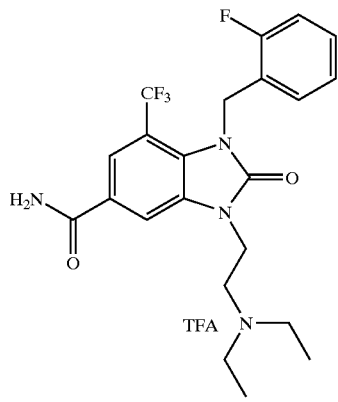

A solution of 3-[2-(diethylamino)ethyl]-2-oxo-7-(trifluoromethyl)-2,3-dihydro-1H-benzimidazole-5-carbonitrile (10.3 mg), 2-fluorobenzyl chloride (0.05 ml) and potassium carbonate (23.8 mg) in N,N-dimethylformamide (1.5 ml) was stirred with heating at 80° C. for 1.5 hours. The reaction mixture was concentrated in vacuo. To the resultant residue was added t-butanol (1.5 ml), and the mixture was stirred with heating at 60° C. To the solution was added powdered potassium hydroxide crashed in mortar (46.7 mg), and the mixture was stirred with heating at 60° C. for 1 hour. To the reaction mixture was added 1N hydrochloric acid, and the mixture was concentrated in vacuo. The resultant residue was purified by HPLC using condition 2 to give the title compound (9.1 mg, 51%).

$^1$H-NMR (DMSO-$d_6$, 300 MHz) δ 1.20 (6H, t, J=7.2 Hz), 3.53–3.56 (2H, m), 4.37–4.39 (2H, m), 5.25 (2H, s), 6.87–6.92 (1H, m), 7.04–7.10 (1H, m), 7.21–7.33 (2H, m), 7.07 (1H, brs), 8.00 (1H, s), 8.18 (2H, br), 9.17 (1H, br). HPLC retention time: 23.82 min (condition 2). FAB-MS: 453(M+H)

Example 14

Synthesis of 3-[2-(diethylamino)ethyl]-1-(3-fluorobenzyl)-2-oxo-7-(trifluoromethyl)-2,3-dihydro-1H-benzimidazole-5-carboxamide trifluoroacetate

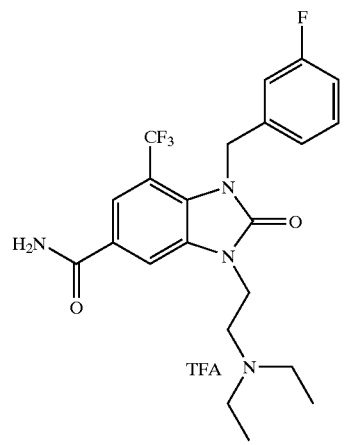

The title compound (10.2 mg, 51%) was prepared from 3-[2-(diethylamino)ethyl]-2-oxo-7-(trifluoromethyl)-2,3-dihydro-1H-benzimidazole-5-carbonitrile (11.6 mg) and 3-fluorobenzyl chloride (0.050 ml) by the procedure similar to that described in Example 12.

$^1$H-NMR (DMSO-$d_6$, 300 MHz) δ 1.22 (6H, t, J=7.2 Hz), 3.24–3.34 (4H, m), 3.50–3.54 (2H, m), 4.38–4.43 (2H, m), 5.22 (2H, s), 6.93–7.08 (3H, m), 7.34 (1H, q, J=6.1 Hz), 7.60 (1H, brs), 7.99 (1H, s), 8.24 (1H, brs), 8.35 (1H, brs), 10.02 (1H, brs). HPLC retention time: 23.64 min (condition 2). FAB-MS: 453 (M+H).

Example 15

Synthesis of 3-[2-(diethylamino)ethyl]-1-(4-fluorobenzyl)-2-oxo-7-(trifluoromethyl)-2,3-dihydro-1H-benzimidazole-5-carboxamide trifluoroacetate

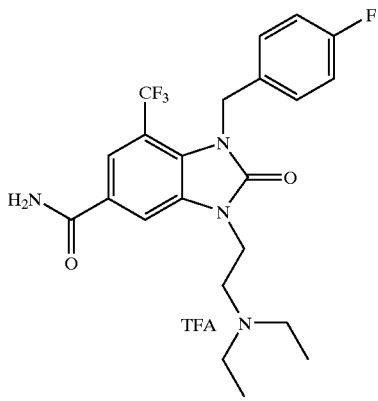

The title compound (3.8 mg, 27%) was prepared from 3-[2-(diethylamino)ethyl]-2-oxo-7-(trifluoromethyl)-2,3-dihydro-1H-benzimidazole-5-carbonitrile (8.0 mg) and 4-fluorobenzyl bromide (0.050 ml) by the procedure similar to that described in Example 12.

$^1$H-NMR (DMSO-$d_6$, 300 MHz) δ 1.20 (6H, t, J=7.2 Hz), 3.50–3.54 (2H, m), 4.32–4.40 (2H, m), 5.21 (2H, s), 7.10–7.20 (4H, m), 7.60 (1H, brs), 7.99 (1H, s), 8.16 (2H, brs), 9.30 (1H, brs). HPLC retention time: 23.87 min (condition 2). FAB-MS: 453 (M+H).

Example 16

Synthesis of 3-[2-(diethylamino)ethyl]-1-(2-methylbenzyl)-2-oxo-7-(trifluoromethyl)-2,3-dihydro-1H-benzimidazole-5-carboxamide trifluoroacetate

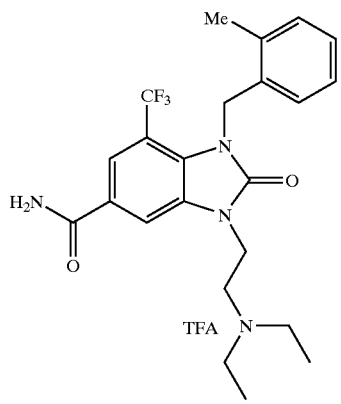

The title compound (11.1 mg, 66%) was prepared from 3-[2-(diethylamino)ethyl]-2-oxo-7-(trifluoromethyl)-2,3-dihydro-1H-benzimidazole-5-carbonitrile (9.7 mg) and 2-methylbenzyl bromide (0.030 ml) by the procedure similar to that described in Example 12.

$^1$H-NMR (DMSO-$d_6$, 300 MHz) δ 1.21 (6H, t, J=7.1 Hz), 2.34 (3H, s), 3.25–3.34 (4H, m), 3.51–3.54 (2H, m), 4.35–4.45 (2H, m), 5.14 (2H, s), 6.53 (1H, d, J=7.7 Hz), 6.98–7.05 (1H, m), 7.13 (1H, t, J=7.7 Hz), 7.21 (1H, d, J=6.8 Hz), 7.60 (1H, brs), 7.98 (1H, s), 8.20 (2H, brs), 9.70 (1H, brs). HPLC retention time: 24.56 min (condition 2). FAB-MS: 449 (M+H)

Example 17

Synthesis of 3-[2-(diethylamino)ethyl]-1-(1-naphthylmethyl)-2-oxo-7-(trifluoromethyl)-2,3-dihydro-1H-benzimidazole-5-carboxamide trifluoroacetate

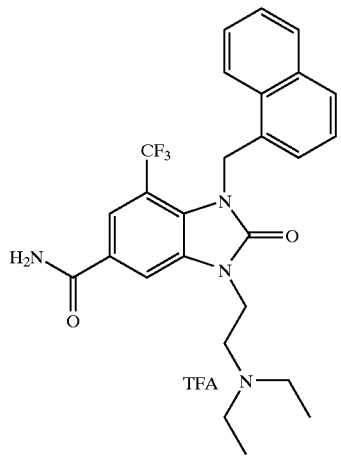

The title compound (4.4 mg, 22%) was prepared from 3-[2-(diethylamino)ethyl]-2-oxo-7-(trifluoromethyl)-2,3-dihydro-1H-benzimidazole-5-carbonitrile (10.8 mg) and 1-(chloromethyl)naphthalene (0.050 ml) by the procedure similar to that described in Example 12.

$^1$H-NMR (DMSO-$d_6$, 300 MHz) δ 0.76–0.89 (6H, m), 3.65–3.68 (2H, m), 4.17–4.23 (2H, m), 5.69 (2H, s), 7.45–7.68 (4H, m), 7.79–7.99 (4H, m), 8.17–8.23 (3H, m), 9.13 (1H, brs). HPLC retention time: 26.27 min (condition 2). FAB-MS: 449 (M+H).

Example 18

Synthesis of 3-[2-(diethylamino)ethyl]-1-(2-naphthylmethyl)-2-oxo-7-(trifluoromethyl)-2,3-dihydro-1H-benzimidazole-5-carboxamide trifluoroacetate

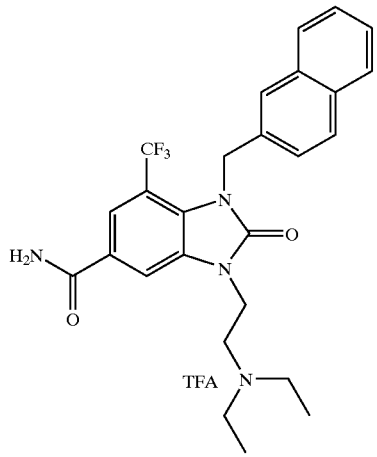

The title compound (10.1 mg, 48%) was prepared from 3-[2-(diethylamino)ethyl]-2-oxo-7-(trifluoromethyl)-2,3-dihydro-1H-benzimidazole-5-carbonitrile (9.7 mg) and 2-(bromomethyl)naphthalene (46.5 mg) by the procedure similar to that described in Example 12.

$^1$H-NMR (DMSO-$d_6$, 300 MHz) δ 0.96 (6H, m), 3.65–3.68 (2H, m), 4.18–4.23 (2H, m), 5.39 (2H, s), 7.33 (1H, dd, J=8.6, 1.8 Hz), 7.43–7.48 (3H, m), 7.55 (1H, brs), 7.72–7.75 (1H, m), 7.85–7.89 (2H, m), 7.96 (1H, s), 8.17–8.23 (2H, brs). HPLC retention time: 26.59 min (condition 2). FAB-MS: 463 (M+H).

Example 19

Synthesis of 1-(2,4-dichlorobenzyl)-3-[2-(diethylamino)ethyl]-2-oxo-7-(trifluoromethyl)-2,3-dihydro-1H-benzimidazole-5-carboxamide trifluoroacetate

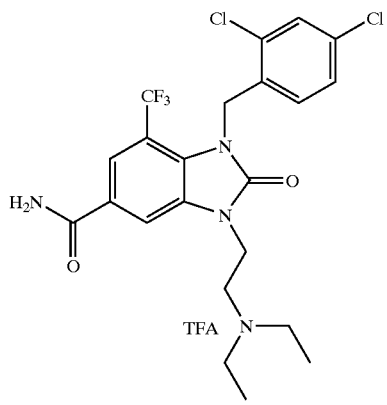

The title compound (3.5 mg, 19%) was prepared from 3-[2-(diethylamino)ethyl]-2-oxo-7-(trifluoromethyl)-2,3-dihydro-1H-benzimidazole-5-carbonitrile (9.7 mg) and 2,4-dichlorobenzyl chloride (66.0 mg) by the procedure similar to that described in Example 12.

$^1$H-NMR (DMSO-d$_6$, 300 MHz) δ 1.19 (6H, t, J=7.2 Hz), 4.34–4.43 (2H, m), 5.18 (2H, s), 6.90 (1H, d, J=8.2 Hz), 7.30 (1H, dd, J=8.2, 2.4 Hz), 7.60–7.63 (1H, m), 7.71 (1H, d, J=2.4 Hz), 8.00 (1H, s), 8.18 (2H, brs), 9.18 (1H, brs). HPLC retention time: 27.93 min (condition 2). FAB-MS: 503 (M+H).

Example 20

Synthesis of 1-(2,5-dichlorobenzyl)-3-[2-(diethylamino)ethyl]-2-oxo-7-(trifluoromethyl)-2,3-dihydro-1H-benzimidazole-5-carboxamide trifluoroacetate

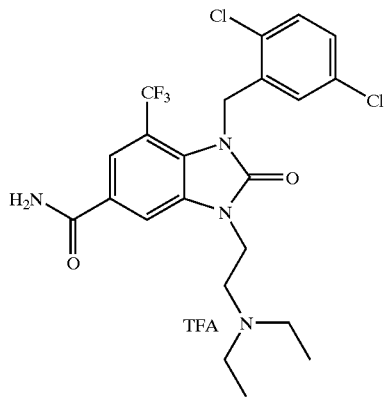

The title compound (3.2 mg, 15%) was prepared from 3-[2-(diethylamino)ethyl]-2-oxo-7-(trifluoromethyl)-2,3-dihydro-1H-benzimidazole-5-carbonitrile (11.6 mg) and 2,5-dichlorobenzyl chloride (110.9 mg) by the procedure similar to that described in Example 12.

$^1$H-NMR (DMSO-d$_6$, 300 MHz) δ 1.21 (6H, t, J=7.2 Hz), 3.53–3.58 (2H, m), 4.35–4.39 (2H, m), 5.17 (2H, s), 7.06 (1H, brs), 7.38–7.42 (1H, m), 7.58 (1H, d, J=8.4 Hz), 7.62 (1H, brs), 8.01 (1H, s), 8.20–8.22 (2H, m), 9.17 (1H, brs). HPLC retention time: 26.84 min (condition 2). FAB-MS: 503 (M+H).

Example 21

Synthesis of 1-[(6-chloro-1,3-benzodioxol-5-yl)methyl]-3-[2-(diethylamino)ethyl]-2-oxo-7-(trifluoromethyl)-2,3-dihydro-1H-benzimidazole-5-carboxamide trifluoroacetate

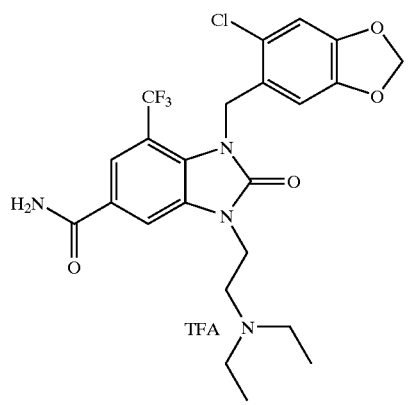

The title compound (6.2 mg, 31%) was prepared from 3-[2-(diethylamino)ethyl]-2-oxo-7-(trifluoromethyl)-2,3-dihydro-1H-benzimidazole-5-carbonitrile (10.5 mg) and 6-chloropiperonyl chloride (46.4 mg) by the procedure similar to that described in Example 12.

$^1$H-NMR (DMSO-d$_6$, 300 MHz) δ 1.18–1.22 (6H, m), 3.54–3.57 (2H, m), 4.33–4.38 (2H, m), 5.09 (2H, s), 6.01 (2H, s), 7.02 (1H, s), 7.16 (1H, s), 7.60 (1H, brs), 8.00 (1H, s), 8.18 (2H, brs), 9.20 (1H, brs). HPLC retention time: 25.51 min (condition 2). FAB-MS: 513 (M+H).

Example 22

Determination of Biological Activity

Benzimidazolidinone derivatives of the present invention were evaluated for their growth hormone (GH) release promoting activity by reference to the method described in a literature (R. G. Smith et al., Science, 260, 1640 (1993)).

Pituitary glands removed from 7-week-old male Wistar/ST rats were washed three times with HBSS(−) and the tissue was minced into small pieces (ca. 1 mm square) using a pair of scissors. The tissues were transferred to a 15 ml round-bottom centrifuge tube and washed three times with HBSS(−) (10 ml). An enzyme solution (0.1 ml per one pituitary gland) was added and enzymatic digestion was started in a water bath at 37° C. During the process, the mixture was pipetted every 5 minutes and the treatment was continued for ca 20–30 min until the cells were dispersed. The resulting cell suspension was centrifuged at 1200 rpm for 2–3 min at room temperature and the supernatant was discarded. A culture medium (8 ml) was added. Similar procedure was repeated twice and the dispersed cells were washed. The cells were plated in a 96-well plate (1×10$^4$ cells/100 μl/well) and incubation was started at 37° C. under 5% CO$_2$ atmosphere.

Three days after the start of the culture, the supernatant was discarded and an assay medium was added. The cells were incubated for 1.5 h and washed once with the assay medium. A test compound solution was added and the cells were reacted at 37° C. for 15 min in an incubator under 5% $CO_2$. The supernatant was recovered and the GH level thereof was measured by RIA.

A sample (50 μl) diluted with RIA buffer (1% BSA, 0.1% $NaN_3$ and 25 mM EDTA/PBS (pH 7.6)), [$^{125}$I]-labeled GH solution (50 μl, ca. 10,000 cpm), and rabbit antiserum (diluted 1,000-fold) against rat GH (50 μl, Biogenesis Co) were placed in each well of a 96-well plate for RIA (Coster Co) and the mixture was reacted for 3 days at 4° C. Cell membrane fractions containing protein A were added and the mixture was allowed to stand for 20 min and centrifuged. The supernatant was recovered and the precipitates were washed with the RIA buffer. The $^{125}$I amount was measured. The GH level of the sample was calculated from the standard curve drawn using the standard GH.

The $EC_{50}$ values (B) were determined by recurrent calculation by inserting the concentration (X nM) of the compound used for the test and the measured GH level, Y (ng/ml), of the test supernatant into the following calculation equation, where A and C are the values obtained by recurrent calculation, C shows GH level of the supernatant in the absence of the compound, and A shows the difference between C and GH level of the culture supernatant when the compound concentration X is infinite:

$Y=AX/(B+X)+C$

The composition of the culture medium was DMEM containing 10% horse serum, 2.5% fetal bovine serum, 1% nonessential amino acids, 1% antibiotics. The composition of the assay medium was 25 mM HEPES/culture medium (pH 7.3). The test compound solution was prepared by adding a compound solution (1 μl), adjusted to 1000-fold concentration with DMSO, to an assay medium (1 ml). Collagenase (400 mg), DNase type I (1 mg), and BSA (1 g) were dissolved in a 25 mM HEPES buffer (pH 7.4, 40 ml) containing 0.8% NaCl, 0.037% KCl, 0.9% glucose, 1% streptomycin-penicillin and 0.7 mM $Na_2HPO_4$, and 1 mg/ml $CaCl_2$ (226 μl) was added. The resulting solution was adjusted to a final volume of 50 ml by adding a HEPES buffer and sterilized by filtration through a 0.22 μm filter and used as the enzyme solution.

Benzimidazolidinone derivatives of the present invention promote the release of growth hormone.

The GH release promoting activity of the compounds of Examples is shown in the following. For the activity, the ratio of GH level of the supernatant in the presence of the test compound (compound concentration 10000 nM) to GH level of supernatant in the absence of the compound (GH level of supernatant in the presence of the compound/GH level of supernatant in the absence of the compound).

TABLE 1

| test compound | GH release promoting activity |
|---|---|
| compound of Example 3 | 1.2 |
| compound of Example 5 | 1.3 |
| compound of Example 7 | 3.0 |
| compound of Example 8 | 2.1 |
| compound of Example 9 | 1.3 |
| compound of Example 16 | 1.0 |

GH release promoting activity = (GH level of supernatant in the presence of the compound)/(GH level of supernatant in the absence of the compound)

INDUSTRIAL APPLICABILITY

Novel benzimidazolidinone derivatives of the present invention and pharmaceutically acceptable salts thereof are growth hormone releaser which are orally applicable, and can be used for stimulation of growth hormone release in the elderly, treating growth hormone deficient adults, prevention of catabolic side effects of glucocorticoids, treatment of osteoporosis, activation of the immune system, acceleration of wound healing, acceleration of bone fracture repair, treatment of growth retardation, treating acute or chronic renal failure or insufficiency, treatment of physiological short stature including growth hormone deficient children, treatment of short stature associated with chronic illness, treatment of obesity and growth retardation associated with obesity, treatment of growth retardation associated with Prader-Willi syndrome or Turner's syndrome, and the like.

This application is based on Japanese Patent Application No. 2001-22352, the entire contents of which are hereby incorporated by reference.

What is claimed is:

1. A benzimidazolidinone derivative of formula (1) or a pharmaceutically acceptable salt thereof:

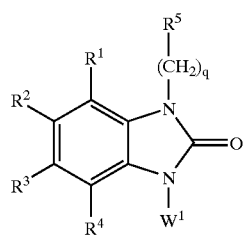

(1)

wherein $R^1$ is optionally substituted $C_1$–$C_3$ alkyl, optionally substituted $C_1$–$C_3$ alkoxy, $C_1$–$C_3$ alkylthio, hydroxy, cyano, halogen or nitro;

$R^2$ is hydrogen, optionally substituted $C_1$–$C_3$ alkyl, optionally substituted $C_1$–$C_3$ alkoxy, hydroxy, cyano or halogen;

$R^3$ is optionally substituted $C_1$–$C_6$ alkyl, optionally substituted $C_3$–$C_7$ alkynyl, optionally substituted $C_1$–$C_6$ alkoxy, carbamoyl, amino, hydroxy, cyano, nitro or halogen;

$R^4$ is hydrogen, hydroxy, cyano, fluorine or chlorine;

q is 0 or 1;

$R^5$ is optionally substituted aryl;

$W^1$ is a group represented by formula (2):

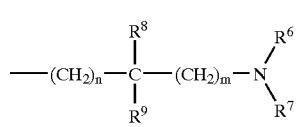

(2)

wherein n is 1, 2 or 3; m is 0, 1, 2 or 3;

$R^6$ and $R^7$ are each independently hydrogen, optionally substituted alkyl or optionally substituted cycloalkyl; or $R^6$ and $R^7$ are taken together to form optionally substituted saturated heterocyclic ring containing nitrogen(s);

$R^8$ and $R^9$ are each independently hydrogen, optionally substituted alkyl or optionally substituted cycloalkyl; or $R^8$ and $R^9$ are taken together to form optionally substituted cycloalkane or optionally substituted saturated heterocyclic ring;

or $R^6$ and $R^8$ are taken together to form optionally substituted saturated heterocyclic ring containing nitrogen(s); or $R^7$ and $R^9$ are taken together to form optionally substituted saturated heterocyclic ring containing nitrogen(s).

2. The benzimidazolidinone derivative or a pharmaceutically acceptable salt thereof according to claim 1 wherein $R^1$ is optionally substituted $C_1$–$C_3$ alkyl.

3. The benzimidazolidinone derivative or a pharmaceutically acceptable salt thereof according to claim 1 wherein $R^1$ is $C_1$–$C_3$ alkyl substituted by halogen(s).

4. A pharmaceutical composition comprising the benzimidazolidinone derivative or a pharmaceutically acceptable salt thereof according to claim 1 and an inactive carrier.

5. The benzimidazolidinone derivative or a pharmaceutically acceptable salt thereof according to claim 1, wherein q=0.

6. The benzimidazolidinone derivative or a pharmaceutically acceptable salt thereof according to any of claims 1–3 and 5, wherein both of $R^2$ and $R^4$ are hydrogen.

7. The benzimidazolidinone derivative or a pharmaceutically acceptable salt thereof according to any of claims 1–3 and 5, wherein $R^3$ is optionally substituted $C_3$–$C_7$ alkynyl or carbamoyl.

8. The benzimidazolidinone derivative or a pharmaceutically acceptable salt thereof according to any of claims 1–3 and 5, wherein $R^5$ is optionally substituted phenyl, optionally substituted 1-naphthyl, or optionally substituted 2-naphthyl.

9. The benzimidazolidinone derivative or a pharmaceutically acceptable salt thereof according to claim 8, wherein $R^5$ is phenyl substituted by alkyl(s), halogen(s), trifluoromethyl(s), or alkoxy(s).

10. The benzimidazolidinone derivative or a pharmaceutically acceptable salt thereof according to any of claims 1–3 and 5, wherein $R^6$ and $R^7$ are each independently optionally substituted alkyl or optionally substituted cycloalkyl; or $R^6$ and $R^7$ are taken together to form optionally substituted saturated heterocyclic ring containing nitrogen(s).

11. The benzimidazolidinone derivative or a pharmaceutically acceptable salt thereof according to any of claims 1–3 and 5, wherein $W^1$ is a group represented by formula (3):

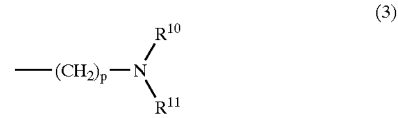

(3)

wherein p is 2, 3, or 4; $R^{10}$ and $R^{11}$ are each independently optionally substituted alkyl.

12. The benzimidazolidinone derivative or a pharmaceutically acceptable salt thereof according to claim 11, wherein $R^{10}$ and $R^{11}$ are each independently methyl or ethyl.

* * * * *